United States Patent
Papa et al.

(10) Patent No.: US 9,207,830 B2
(45) Date of Patent: Dec. 8, 2015

(54) PHYSICAL HEALTH APPLICATION AND METHOD FOR IMPLEMENTATION

(71) Applicants: Eduard Papa, Drexel Hill, PA (US); Vladimir Nestoyanov, Philadelphia, PA (US)

(72) Inventors: Eduard Papa, Drexel Hill, PA (US); Vladimir Nestoyanov, Philadelphia, PA (US)

(*) Notice: Subject to any disclaimer, the term of this patent is extended or adjusted under 35 U.S.C. 154(b) by 210 days.

(21) Appl. No.: 13/632,934

(22) Filed: Oct. 1, 2012

(65) Prior Publication Data
US 2013/0091454 A1    Apr. 11, 2013

Related U.S. Application Data

(60) Provisional application No. 61/543,873, filed on Oct. 6, 2011.

(51) Int. Cl.
| | | |
|---|---|---|
| G06F 3/048 | (2013.01) | |
| G06F 3/0484 | (2013.01) | |
| G06F 3/0481 | (2013.01) | |
| G06F 9/44 | (2006.01) | |
| G06F 3/0486 | (2013.01) | |
| G06F 11/32 | (2006.01) | |

(52) U.S. Cl.
CPC .............. *G06F 3/048* (2013.01); *G06F 3/0481* (2013.01); *G06F 3/0484* (2013.01); *G06F 3/0486* (2013.01); *G06F 3/04817* (2013.01); *G06F 3/04842* (2013.01); *G06F 3/04845* (2013.01); *G06F 3/04847* (2013.01); *G06F 9/4446* (2013.01); *G06F 11/323* (2013.01)

(58) Field of Classification Search
CPC . G06F 3/0484; G06F 3/0481; G06F 3/04817; G06F 3/04842; G06F 3/04847; G06F 9/446; G06F 3/0486; G06F 11/323; G06F 3/04845
See application file for complete search history.

(56) References Cited

U.S. PATENT DOCUMENTS

| | | | |
|---|---|---|---|
| 2009/0143994 A1* | 6/2009 | Barnett et al. | 702/19 |
| 2010/0036662 A1* | 2/2010 | Emmons | 704/235 |
| 2010/0080875 A1* | 4/2010 | Miller-Kovach et al. | 426/232 |
| 2010/0179027 A1* | 7/2010 | McGlynn et al. | 482/9 |
| 2010/0179833 A1* | 7/2010 | Roizen et al. | 705/3 |
| 2010/0273610 A1* | 10/2010 | Johnson | 482/9 |

* cited by examiner

*Primary Examiner* — William Bashore
*Assistant Examiner* — James F Sugent
(74) *Attorney, Agent, or Firm* — Mendelsohn, Drucker & Dunleavy, P.C.

(57) ABSTRACT

A physical health application is accessible via a computer network. The application has a dynamic user interface with an interactive chart. The interactive chart displays a physical parameter over time. The interactive chart is adapted to set a physical progress goals.

24 Claims, 29 Drawing Sheets

PHYSICAL HEALTH APPLICATION AND METHOD FOR IMPLEMENTATION

This non-provisional application claims the benefit of the U.S. PTO provisional application 61/543,873 filed on Oct. 6, 2011

BACKGROUND OF THE INVENTION

1. Field of the Invention

The field of the invention is directed towards computer applications. In particular, the field of the invention is directed towards a physical health application.

2. Description of the Related Technology

The manual process of managing personal fitness and diet is time consuming and prone to error. To do so, individuals need to keep daily track of their fitness parameters, such as weight, fat level, age, re-estimate their activity level; recalculate caloric intake and expenditure; design custom meal plans and maintain food logs, etc. These activities involve calculations and extensive record keeping.

Mathematical equations involved in this process are complicated and are not easily accessible for an individual. It is hard to understand whether BMR, RMR, or EER caloric intakes should be consumed; what the impact is of changing activity level on previously calculated intakes; and how to factor in daily weight change into initially calculated intakes, etc. The level of effort required is evident after reading the Dietary Reference Intakes from National Academy of Sciences, which is the government standard for nutritional and dietary guidelines.

Another consideration stems from an abundance of misrepresentative information available from informal media sources such as magazines and the Internet. Often individuals are lead to rely on knowledge of BMI without realizing the higher importance of fat level, following fad advice on amounts and composition of a diet, ignoring the dynamic nature of dietary process (e.g. numbers estimated for the same individual at the beginning may no longer be valid some time later due to change in weight and other parameters), and jumping into planning their fitness and diet without understanding the core physiological processes, etc.

Therefore there is a need in the field to provide a comprehensive physical health application able to simplify the dieting process in a comprehensive and healthy manner.

SUMMARY OF THE INVENTION

An object of the present invention may be a physical health application.

Another object of the present invention may be a method for tracking physical health.

Still yet another object of the present invention may be an interactive chart.

Still another object of the present invention may be a physical health application interactive with a social network.

An aspect of the present invention may be a physical health application accessible via a computer network comprising: a dynamic user interface comprising an interactive chart; wherein the interactive chart displays a physical parameter over time; and wherein the interactive chart is adapted to be adjusted to set a physical progress goal.

Another aspect of the present invention may be a method for tracking physical health via a computer network application comprising: displaying a physical parameter over time on a dynamic user interface comprising an interactive chart; and adjusting a physical progress goal on the interactive chart.

Still yet another aspect of the present invention may be a method of optimizing a user interface comprising; rendering the interface at high frequency when interacting slowly with the interface; and rendering the interface at low frequency when interacting rapidly with the interface.

Another aspect of the present invention may be an interactive user interface comprising: means reducing lag time, wherein the means for reducing lag time renders the interface at high frequency when interaction with the interface is slow; and renders the interface at low frequency when interaction with the interface is rapid.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
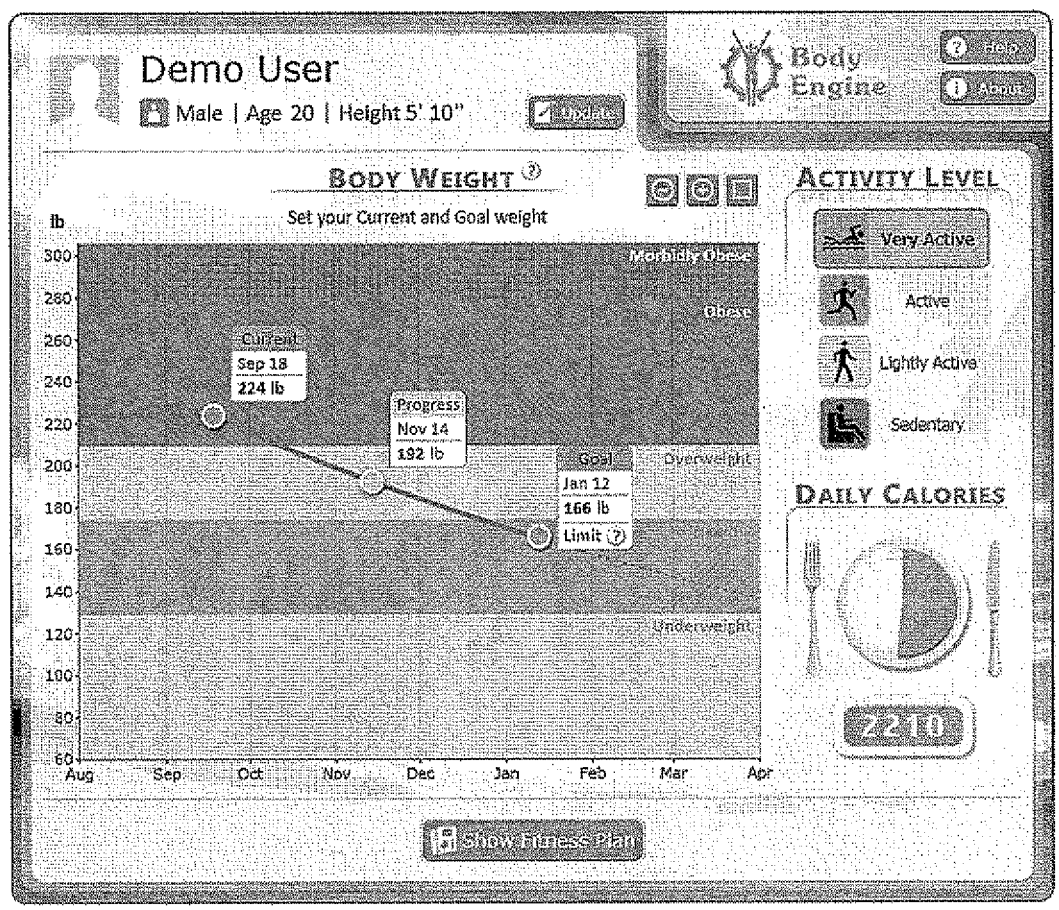
FIG. 1 shows the main window of the graphical user interface used in an embodiment of the present invention.

The system and method for providing a physical health application employs an interactive chart. The application is referred to as BodyEngine herein. BodyEngine uses fitness and diet formulas established by the Institute of Medicine of the US Government and accepted by the wider fitness science community. The fitness formulas are combined with innovative computer algorithms to accurately calculate a fitness plan that permits the user to progress to his/her goal fitness state at any time in the future. In order to protect the user from setting an unhealthy goal, BodyEngine ensures the user's goal falls within a safe and realistic zone. The system and method may be used and employed on networks, computers and/or mobile devices.

BodyEngine's highly interactive graphical user interface is intuitive and easy to use for anyone. The application comprises unique dynamic fitness components that allow the user to see the immediate effects of his/her interaction in real-time as opposed to filling out data forms and then updating the state. The user may easily set his/her current and goal weight and/or fat level by intuitively dragging and dropping selection sliders integrated into 2-dimensional charts, each displaying three data dimensions: weight, time, and color-coded BMI OR fat level, time, and color-coded fat levels. Similarly, the user can select his/her activity level with a single touch and immediately see the effects it has on his/her future progress and the number of daily calories, which the application visually represents as a plate of food.

The fitness plan created by the BodyEngine application is personalized based on the user's personal information such as gender and height; and fitness specific information such as current and goal fitness state; and activity level indicated by the user. The plan shows the user how to reach his/her goal fitness state and provides the daily requirements for activity level and calories. Additionally, the plan provides statistics about the user's current and goal BMI, the total weight lost, the weekly rate of the weight loss, the required calories, calories proportion, and calories deficit. The user can choose to share his/her fitness plan with his friends on Facebook.

BodyEngine provides the user with the answer to the question "Considering my current personal parameters (gender, height, age, etc.), life style preferences, and current fitness state, if I want to reach a specific fitness state by a specific date, what should my daily calories intake be?"

BodyEngine displays an interactive chart based on weight, time, and BMI, which can be used independently or in conjunction with a similar chart based on Fat Level and Time.

Referring to FIGS. 5-18, the weight chart represents three dimensions of data: weight—starting at a minimum of 60 pounds and up to a maximum of 400 pounds; time—starting M months or more in the past and continuing N months or more in the future; and BMI Level—colored zones showing underweight, healthy, overweight, obese, morbidly obese BMIs The purpose of the weight chart is to: input current weight at the current date, i.e. "weigh-in", whenever the user wants to bring data up to date (otherwise current weight is estimated based on previously set goal); input goal weight; input goal date when to reach the goal weight; input pace/rate at which to lose weight; see progress from current weight to goal weight; see the current and goal BMI fitness state (underweight, healthy, overweight, obese, morbidly obese) on colored zones (yellow, green, yellow, red, bright red); see safety limits for the goal (dotted lines of the selection zone); and see weight progression in the past 2-3 months and future months.

The weight chart is updated by changes to: user interaction (click, drag and drop, mouse over); personal information (age, gender, height); activity level; fat level chart (because fat level and weight charts are synchronized); selection zone (e.g. sliders are coerced by selection zone); and zoom level (zoom in, zoom out, zoom optimal).

Changing current weight updates the following: the weight line rendered on chart; the selection zones in weight chart and fat level chart; the goal weight selected on chart; the goal fat level shown on fat level chart; the current fat level shown on fat level chart (charts synchronization); and the number of calories needed to reach goal weight.

Figure 19:
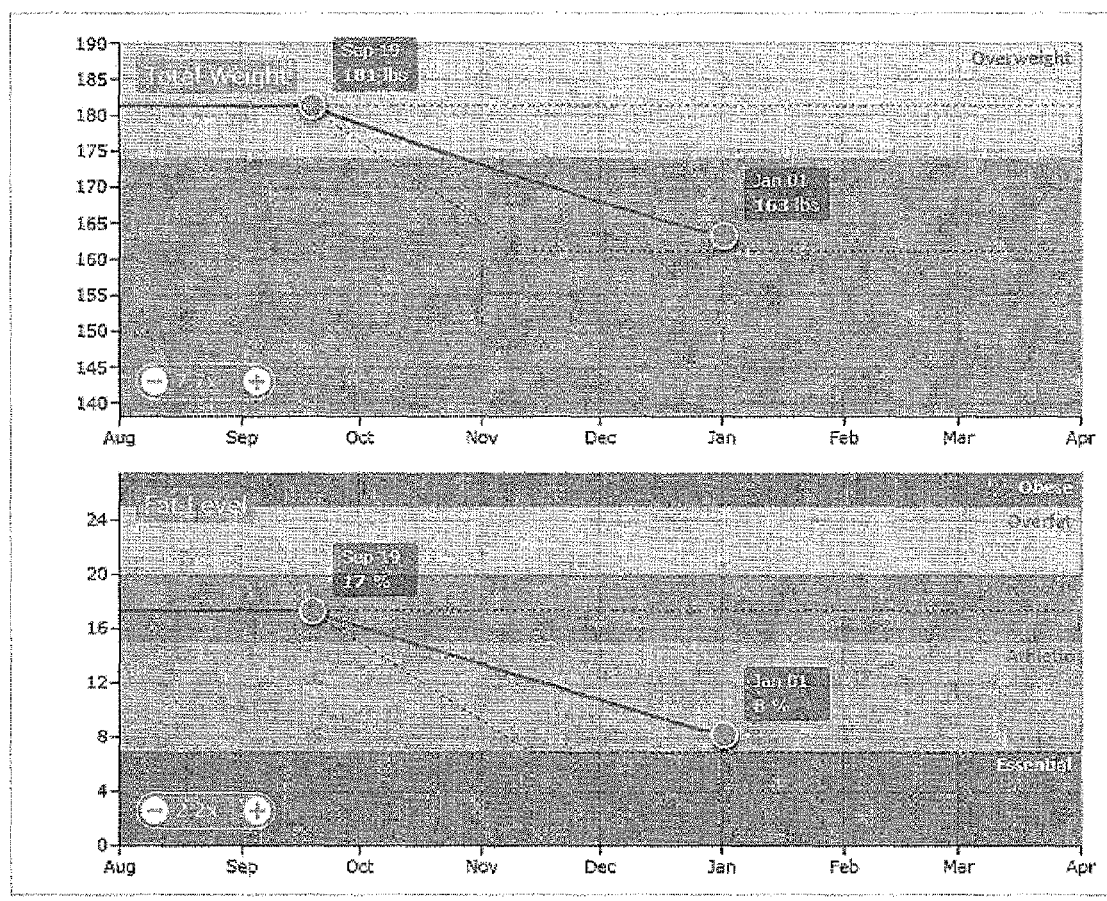
FIG. 19 shows an overall fat level chart, used in an embodiment of the present invention.
Figure 20:
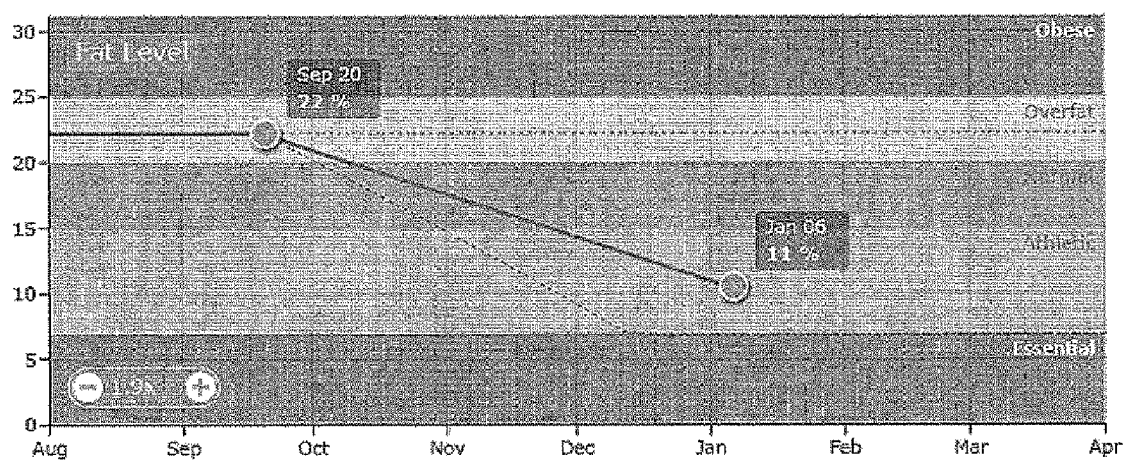
FIG. 20 shows fat level color zones for a fat level chart, used in an embodiment of the present invention.

Changing goal weight updates the following: the weight line rendered on chart; the date when the goal weight will be reached; the date when the goal fat level will be reached; the goal fat level shown on fat level chart; and the number of calories needed to reach goal weight Referring to FIGS. 19-20, the fat level chart represents three dimensions of data; fat level—starting at 0 and up to 60+%; time—starting M months or more in the past and continuing N months or more in the future. fat level zones— colored zones showing underweight, essential, athletic, healthy, overweight and obese fat levels in different colors.

The purpose of the fat level chart is to: input current fat level as a percentage of weight specified in the weight chart, i.e. "weigh-in" the body fat level; input goal fat level as a percentage of goal weight; input goal date when to reach the fat level; input pace/rate at which to lose the fat level; see progress from current fat level to goal fat level; see the current and goal fat level state (underweight, healthy, overweight, obese, morbidly obese) on colored zones (yellow, green, yellow, red, bright red); see safety limits for the goal (dotted lines of the selection zone); and see weight progression in the past 2-3 months and future months The fat level chart is updated by changes to: user interaction (click, drag and drop, mouse over); personal information (age, gender, height); activity level; the weight chart (charts synchronization); goal selection zone (sliders coercion); and zoom level (zoom in, zoom out, zoom optimal).

Changing current fat level updates the following: the fat level line rendered on chart; the selection zones in weight and fat level charts; the goal weight (charts synchronization); the goal fat level; and the number of calories needed to reach the goal weight (while preserving original FFM (fat-free mass).

By changing goal fat level updates this changes: the fat level line rendered on chart; the date when the goal fat level will be reached; the date when the goal weight will be reached; the goal weight shown on weight chart; and the number of calories needed to reach the goal weight (while preserving original FFM (fat-free mass).

Referring to FIGS. 19 and 20, the weight and the fat level charts are very similar to each other in how they interact with the user. They are both made up of current and goal sliders to set the current and goal fitness state values. Both of them render a progress line, have stacked color zones, and selection zones. The differences between the charts are the formulas used to render them. The weight chart renders the user's weight and shows the color zones based on BMI while the fat level chart renders the user's fat level and shows the color zones based on fat level categories.

One of the most important aspects of the two charts is that they interact with each other. Making changes to one affects the other and vice versa. For example, if the user has set his weight at 200 lb and fat level at 25% and he moves the total weight down to 198 lb, the fat level will be adjusted to 24%, while the original FFM (fat-free mass) remains the same until the user explicitly adjusts the fat level slider. The goal weight has a similar relationship with the goal fat level. Other relationships exist between the charts.

The sliders are positioned on top of a chart and point to a single (x,y) coordinate (see FIG. 7 and FIG. 8) where the X-coordinate is the date and the Y-coordinate is the body weight (or fat level % on Fat Level Chart). For BodyEngine, the user moves them around to select the weight, fat level, and time coordinates. Sliders are activated when the user touches them with the pointer and they can be moved around by drag-and-drop actions.

The progress line shows the user's weight or fat level progression from his past to current, current to goal, and goal to future (see FIGS. 6-11). The set goal can extend to some undefined date in the future indicating that no change is intended past the goal point. The user can click on the progress line to see the value at the specific coordinate he clicks on (See FIG. 11).

TABLE 1

Progress Line Algorithm

```
function populateProgressLine( )
    array[ ] progressLine = new array[days between current and goal
    date]
    progressiveWeight = currentWeight
    for i from current date until goal date incremented by 1 day
        progressiveLine[i] = progressiveWeight
        eerCurrent = compute EER for progressive weight
        caloriesDeficit = eerCurrent − selectedCalories
        progressiveWeight = progressiveWeight − (caloriesDeficit /
        3500)
    return progressiveWeight
```

The selection zone is an area of the chart with dashed borders (see FIGS. 12-15).

The selection zone is an important feature of BodyEngine. The purpose of the selection zones is to limit the user's goal selection in the weight or fat level charts to within safe and realistic ranges. The selection zone is shown only when the user touches the sliders or the activity level.

The lower limit is determined by the maximum of: The weight progression after consuming N calories where N is determined by the Resting Metabolic Rate (RMR) for the user's current weight; the essential fat level limit; and the underweight BMI limit.

The upper limit for goal weight is determined by the current total weight. The upper limit for fat level is determined by the current fat level.

The selection zone is updated dynamically when the user updates current weight, fat level, age, gender, height, and activity level.

When the selection zone is updated, it ensures that the goal sliders fall within the boundaries. If the sliders fall outside of the boundaries of the selection zone, they are automatically coerced within the boundaries and a limit indicator is shown (See FIG. 16).

If the goal sliders are coerced by the borders of the selection zone, a label is added to the sliders to let the user know that his goal is limited. The user can put the mouse over the limit to see why it is limited or click on the context-sensitive help button to open the help section that explains the reasons in detail.

The zoom features of BodyEngine include (see FIG. 18): zoom in; zoom out; zoom optimal—zoom in or out to an optimal view of the chart which allows the current and goal sliders to be in view and in a position where they can be adjusted easily; dynamic zoom—zoom in or out while the user is moving the current or goal sliders. This allows the user to move the sliders freely with a single click and drag, without having to adjust the zoom level.

TABLE 2

Zoom Algorithm

1. Upon user's action to either zoom in or out the chart vertically
2. Detect distance along Y-axis (weight) between the value which corresponds to the bottom edge of the chart area and the value which corresponds to the top edge of the chart (i.e. visible chart height)
3. Detect distance along Y-axis (weight) between the value which corresponds to the position of the current fitness state slider and the goal fitness state slider (i.e. selection zone height, from top down to the goal fitness state slider's position)
4. Compute a zoom factor value based on the ratio between these two distances
5. For zoom in, reduce the visible chart height proportionally to the zoom factor, while not exceeding the distance between fitness state sliders
6. For zoom out, increase the visible chart height proportionally to the zoom factor, while not exceeding the maximum supported range of values along the Y-axis (e.g. weight, from 0 lb up to 400 lb).
// For optimal zooming, set visible chart height to the value slightly greater than the vertical distance between fitness state sliders; this results in the maximum zoom-in while still showing interactive area within selection zone for the user to adjust fitness state sliders.

1. When users moves a fitness state slider to the edge of the visible chart area, initiate automatic one-directional zooming out.
2. If current fitness state slider is moved to the top edge of the visible chart area, chart zooms out while increasing the height of visible chart area by incrementing the Y-axis value which corresponds to the top edge of the chart.
3. If goal fitness state slider is moved to the bottom edge of the visible chart area, chart zooms out while increasing the height of visible chart area by decrementing the Y-axis value which corresponds to the bottom edge of the chart.

As the user moves the sliders integrated into the chart, the chart needs to be rendered as fast as possible in order for the user to see the changes immediately, without any lag. However, rendering is a very intense process that cannot keep up with the movement of the mouse because the user can move the mouse at very fast speeds and the rendering process takes longer. Therefore, BodyEngine incorporates an innovative algorithm that makes the chart more responsive while adapting the rendering frequency to the real-time load and capacity of the computer. It should be understood that references to mouse, may also include other devices that interact with the computer screen and interactive interfaces, such as the use of touch screens, etc.

The optimization algorithm reduces lag from the time the user moves the mouse until he sees the changes on the chart. When the user moves the slider slowly, the chart will be rendered at a higher frequency, and when the user moves the mouse faster, the chart will be rendered at a lower frequency. This makes the chart more responsive and reduces lag without reducing the visual appearance of the chart.

Secondly, the algorithm adapts the rendering frequency of the chart to the performance capacity of the computer. As the computer becomes overloaded (e.g. Antivirus starts scanning for viruses) the algorithm will decrease the rendering frequency and when the computer speeds up again (e.g. Antivirus stops scanning for viruses), the optimizer will increase the rendering frequency. The adaptable nature of the algorithm happens in real-time.

When the user stops moving the mouse, the algorithms causes the chart to be rendered one last time to ensure that the chart reflects the last user interaction. Without this additional feature, there would be times when the last mouse interaction would not be handled by the chart and the user's mouse and the slider would be out of sync.

The rendering optimization described above and implemented for BodyEngine can be applied generally for any computer process or task that is event based and/or needs to adopt its processing rate to the performance and capacity of the computer in which it is running. For example, a computer game or video player can use this algorithm to adapt the frame rate depending on the load of the computer so that it does not overload the computer and cause the game to be choppy.

TABLE 4

Algorithm to Reduce Lag

```
// The duration of the last task that was executed
lastDuration = 0
// The last time a task was executed
lastStartTime = currentTime
// The delay factor is used to control the time when the next task will
// be executed by the algorithm. A delay of 1.0 means that another task
// will be allowed to be executed as soon as the duration of the last task
// expires. A number less than 1.0 will cause the new task to be executed
// while the other one has not finished executing. A number greater than
// 1.0 will cause the task to be executed with a delay equal to
// ((delayFactor − 1.0) * lastDuration).
delayFactor = 1.0
// This delay controls the time after the last handled event which will
// trigger the last execution of the task
lastExecutionDelay = 300 ms
function handleEvent
    triggerAfter(lastExecutionDelay)
    if (currentTime − lastStartTime) > (lastDuration * delayFactor)
        lastStartTime = currentTime
        doWork( )
        lastDuration = currentTime − lastStartTime
function triggerAfter(lastExecutionDelay)
    call(doWork) at (currentTime + lastExecutionDelay)
function doWork
    // render chart
    // render video frame
    // any other task
```

The daily calories are presented as a plate of food (see FIGS. 23-28). The food pie chart represents the daily constant number of calories required to reach the goal weight as a proportion of the calories required to maintain the current weight. The radius of the food pie chart shown on the plate increases or decreases based on the activity level (e.g. if activity level is Very Active, the pie chart will expand to fill the plate and if activity level is sedentary it will contact to a smaller shape).

The calories calculated by BodyEngine are constant from the current date until the goal date. This feature makes it easy for the user to remember and convenient to adopt in his daily routine.

The daily calories are computed with a trial-and-error algorithm which starts with a list of possible answers and applies a recursive binary-search algorithm to narrow down the list to a single answer. The list of answers starts from the EER of the current weight to the RMR of the current weight. The answer is a single caloric value that allows the user to reach his goal weight by the goal date.

TABLE 5

Daily Calories Calculation Algorithm

```
bmr = computeBMR( )
eer = computeEER( )
selectedValue = findCalories(bmr, eer, eer)
function findCalories(minimum, maximum, selectedValue)
    reachableWeight = determineReachableWeight(selectedValue)
    if reachableWeight = goalWeight
        return selectedCalories;
    else if reachableWeight < goalWeight
        return findCalories(selectedValue, maximum, selectedValue / 2)
    else
        return findCalories(minimum, selectedValue, selectedValue / 2)
function determineReachableWeight(selectedCalories)
    progressiveWeight = currentWeight
    from current date until goal date
        eerCurrent = compute EER for progressive weight
        caloriesDeficit = eerCurrent − selectedCalories
        progressiveWeight = progressiveWeight − (caloriesDeficit /
        3500)
    return progressiveWeight
```

The activity level is made up of a set of color-coded icons representing different levels of activity, as specified in the DRI document of the Institute of Medicine (see FIG. 1). The activity levels are ordered by intensity and duration from top to bottom, starting from the topmost Very Active Level down to the Sedentary level. Toggling the activity level affects the calories required to reach the selected goal.

When the user touches the activity level component, the selection zone lines are shown on the chart because they are based on the activity level and changing the activity level affects the selection zone.

Figure 24:
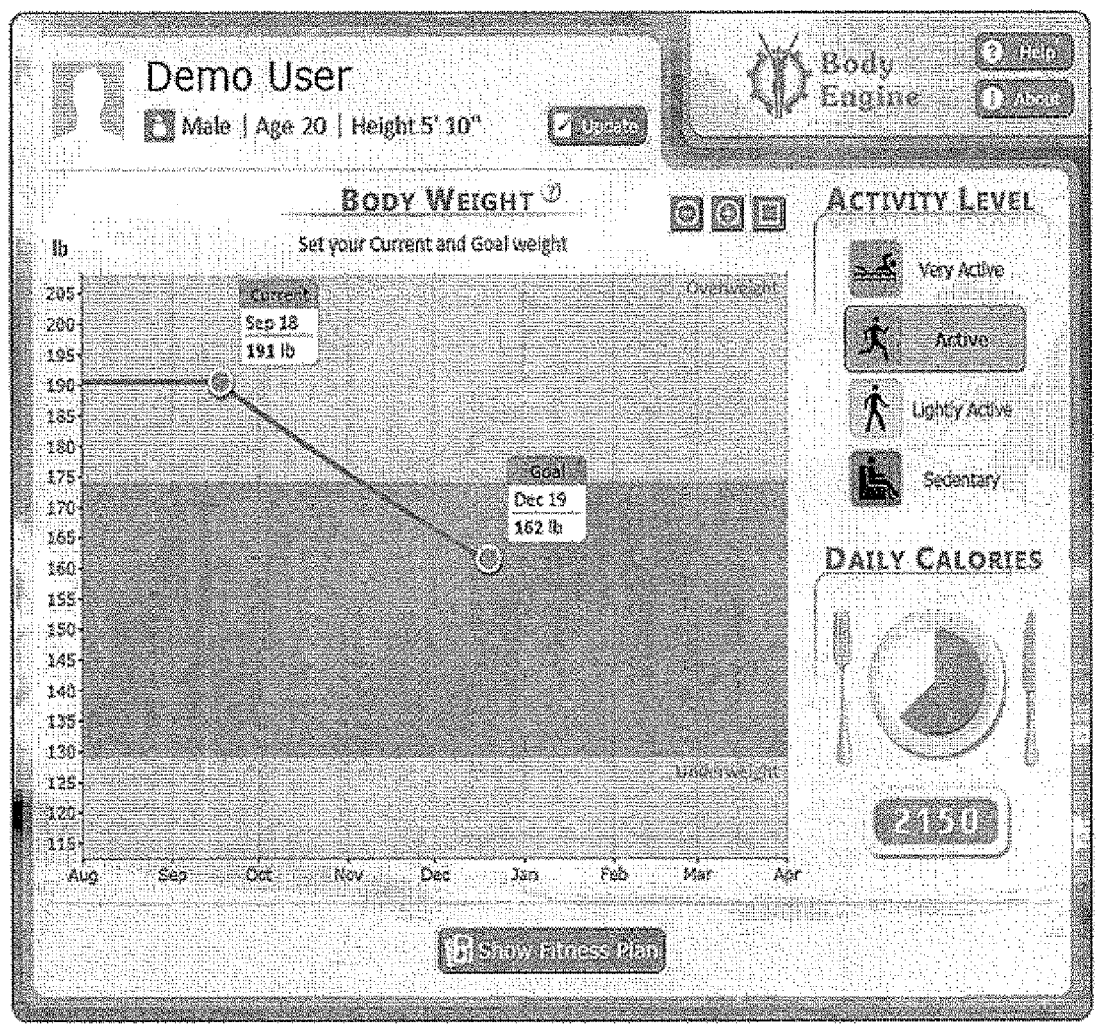
FIG. 24 shows the pie chart for the daily plate, used in an embodiment of the present invention.

When the activity level changes: the selection zone gets updated; the goal weight and goal fat sliders might be coerced by the limits of the selection zone; the calories number will be updated and the calories plate shape will be updated (see FIG. 24).

The fitness plan screen shows the user's (see FIG. 2): current fitness state (weight and BMI at present date); goal fitness state (desired weight and BMI at selected goal date); plan duration in total number of days and split in months, weeks, days; total weight which will be lost by the time goal is reached; rate of weight loss per week; activity level; number of calories to consume to reach the goal fitness state; proportion of calories to consume to reach goal v. calories consumed to maintain current weight; number of calories to cut from the number of calories required to maintain the current weight to induce caloric deficit which leads to a gradual weight loss.

Figure 3:
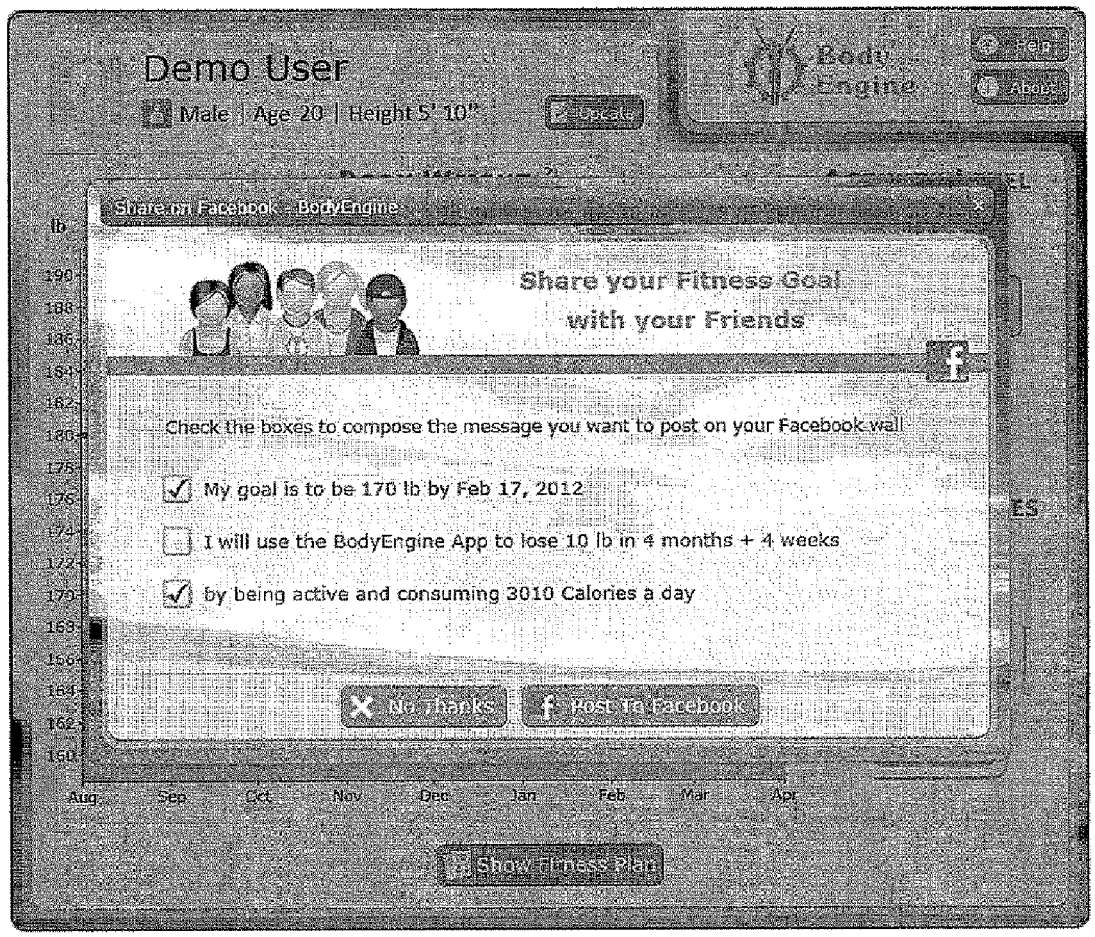
FIG. 3 shows an application graphical user interface for Facebook sharing, used in an embodiment of the present invention.

When BodyEngine is loaded within Facebook, a few social networking features are enabled to integrate BodyEngine with Facebook (see FIG. 3). These features include: retrieving the user's name, gender, birthday and profile picture from Facebook to minimize the data he has to enter and improve his user experience; and give the user the ability to share a customized message with his Facebook friends through BodyEngine. The user can share: his goal weight and goal date; number of pounds lost and the time it will take him to lose it; the number of calories he needs to consume and the activity level.

These social networking features allow BodyEngine users to be motivated and encouraged by their friends because several studies have shown that people who have such support are the most successfully at reaching and maintaining their fitness goals.

Now referring in particular to the figures and referring to FIG. 1 in particular, the figure shows the main UI window presented to the user when application loads, showing interactive Body Weight Chart and sliders (center); activity level buttons (top right); daily plate display with pie chart and calories intake counter (bottom right); and user's personal information panel (top left).

Figure 2:
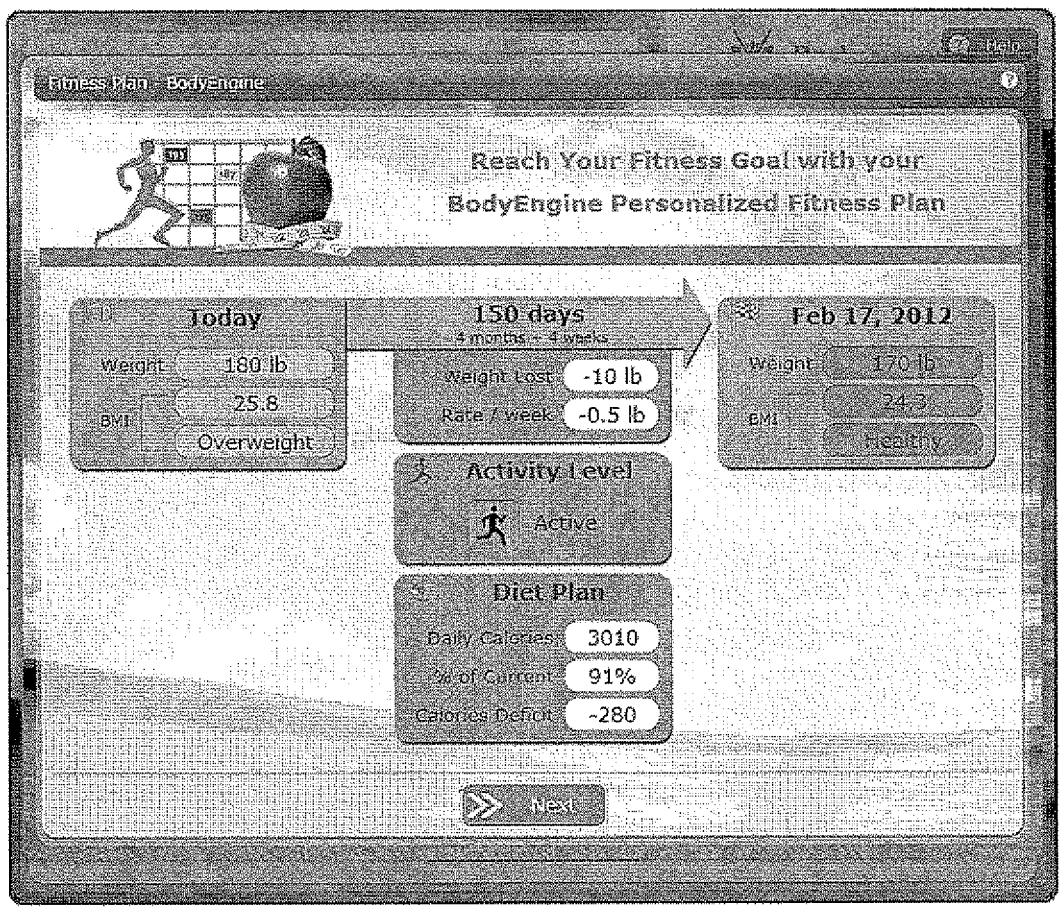
FIG. 2 shows an application graphical user interface for the fitness plan, used in an embodiment of the present invention.

Referring to FIG. 2, fitness plan window is displayed as a pop-up over the main UI window. Shown are current fitness state (labeled with "Today" header); goal fitness state (labeled with "Feb. 17, 2012" header); progress arrow (with count of days to reach goal fitness state); progress statistics (underneath progress arrow); and progress activity and dietary requirements (labeled with "Activity Level" and "Diet Plan" headers).

Referring to FIG. 3, share on Facebook window is displayed as a pop-up over the main UI window. Shown are individual messages, which can be combined into a summary fitness status message to be posted on the user's Facebook wall.

BodyEngine comes with a complete Help document that helps the user to understand how BodyEngine works and how to use it properly.

Figure 4:
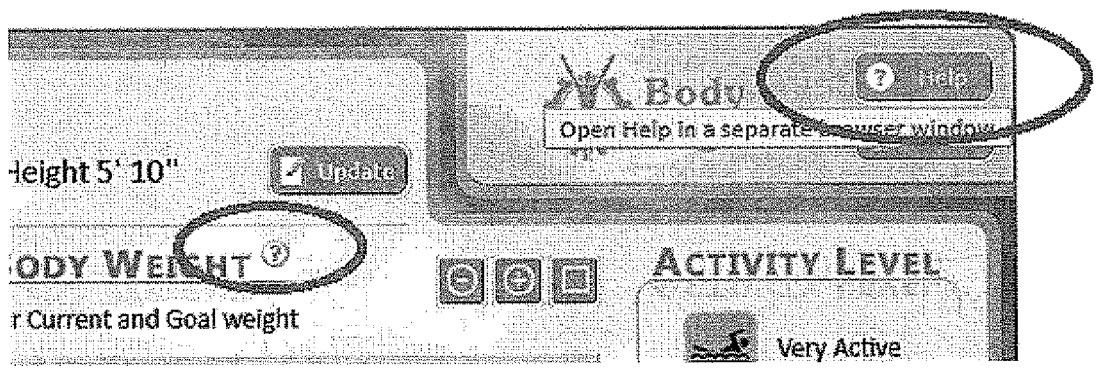
FIG. 4 shows an application graphical user interface showing context sensitive help, used in an embodiment of the present invention.

Referring to FIG. 4, the user can access help either by clicking on the Help button on the main screen, or by clicking on the context-sensitive help icons labeled with a question mark which will open the Help section that talks about that specific component.

Figure 5:
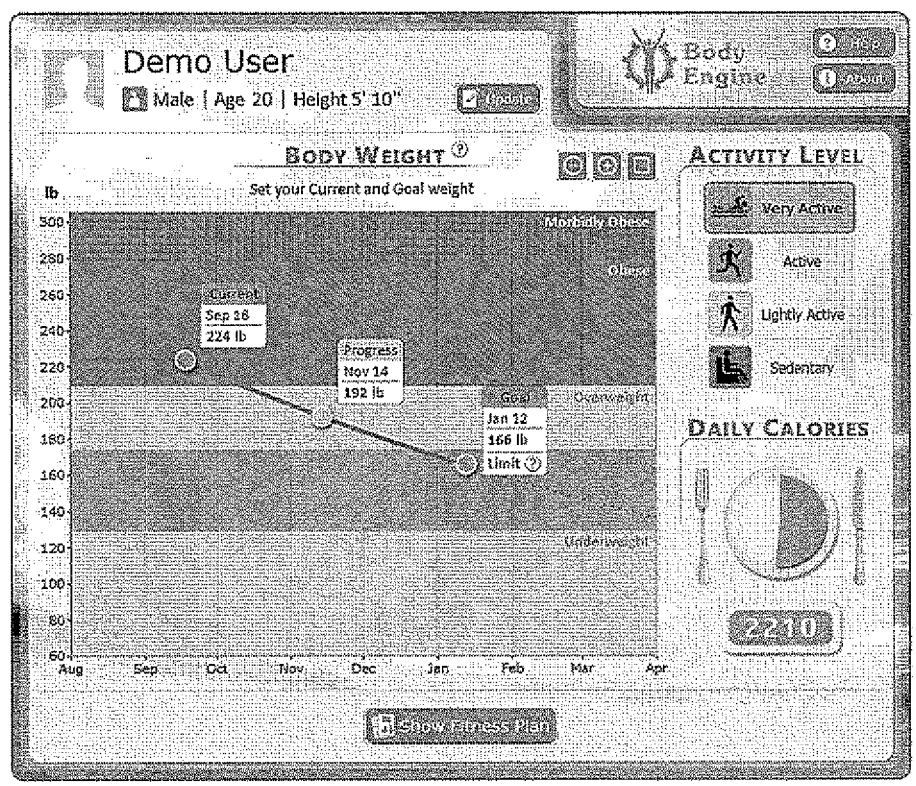
FIG. 5 shows an overall body weight chart, used in an embodiment of the present invention.

Referring to FIG. 5, body weight chart with weight in pounds (Y-axis); time range (X-axis); current weight slider (blue circle with a callout); goal weight slider (orange circle with a callout); progress line (dark bold line) with past progress shown to the left of current weight slider and future progress shown to the right of the current weight slider all the way to the goal weight slider; a progress state (gray circle with a callout) at a given point on the future progress line; selection zone (thin dashed line); selection zone limit state applied to the goal slider (red limit caption); color zones with captions representing BMI levels (color background areas and captions on the right side).

A progress line is an element of the chart which consists of four part: past progress line, current state slider, future progress line (between current and goal state), and goal state slider.

Figure 6:
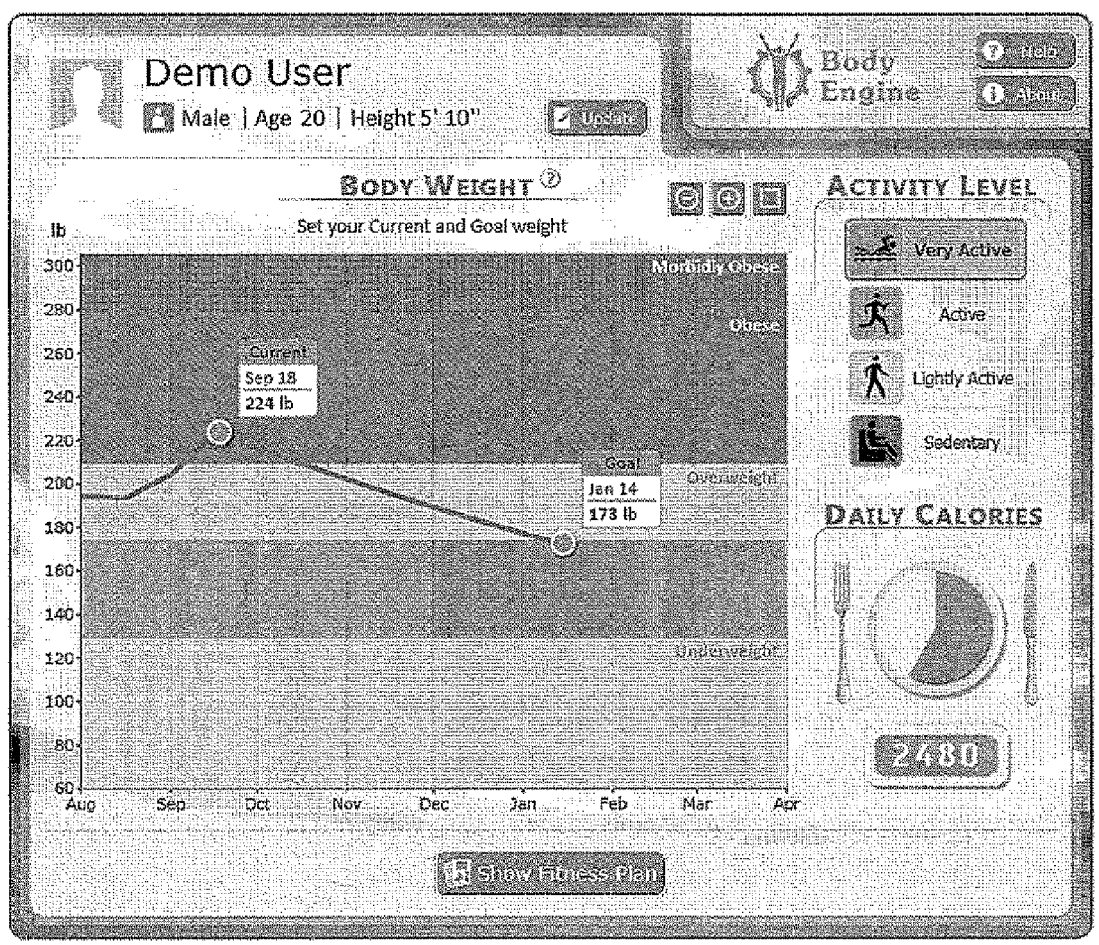
FIG. 6 shows a past progress line on a body weight chart, used in an embodiment of the present invention.

Referring to FIG. 6, a body weight chart with the past progress line extending from the oldest date is displayed by the chart (August 1) to the present date (September 18), displaying user's gradual total body weight change from 195 lb on August 1, to 193 lb on August 15, to 204 lb on September 2, to 224 lb on September 18. Note that if line is straight that means the user's weight has stayed constant for the period covered by the past progress line.

When the user "weighs-in" upon launching an application by adjusting the current state slider, the last segment of the past progress line (September 2-present date) is automatically rendered between the last time the user weighed-in (September 2) and the position of the current state slider. Past progress line segments prior to this segment are static at this point and can no longer be changed.

Figure 7:
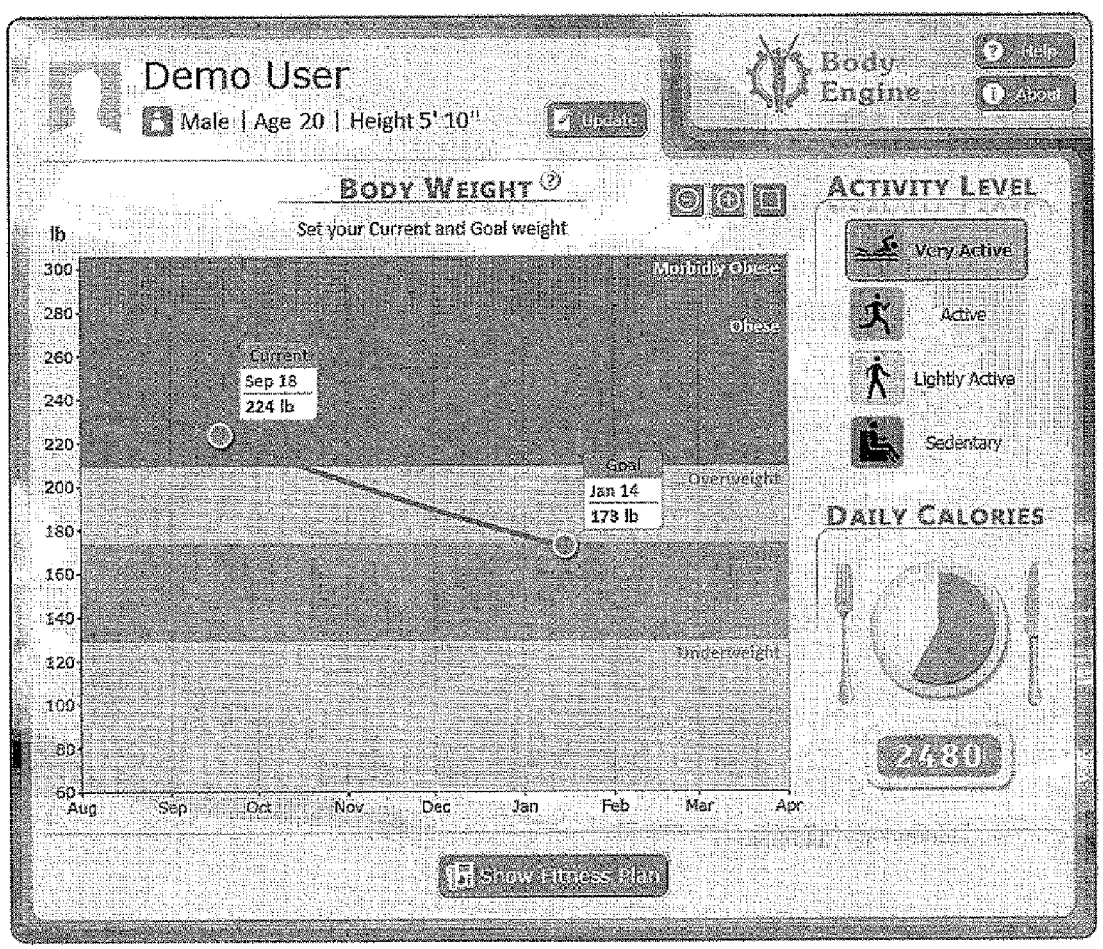
FIG. 7 shows a current weight slider on a body weight chart, used in an embodiment of the present invention.

Referring to FIG. 7, the body weight chart is displayed with the current state slider (blue circle with a callout) representing user's total body weight (Y-axis) as of September 18 (X-axis) which is the present date in this example. Slider's callout displays both the present date and the body weight, and along the time range X-axis is positioned relative to location of the present date (September 18). Past progress line displays a segment from September 1 to present indicating weight change from 230 lb to 224 lb. At this point the user is able to move the current state slider up or down to "weigh-in", in which case the line segment would extend from the 230 lb on September 1 to the user's selected lb value of September 18.

Figure 8:
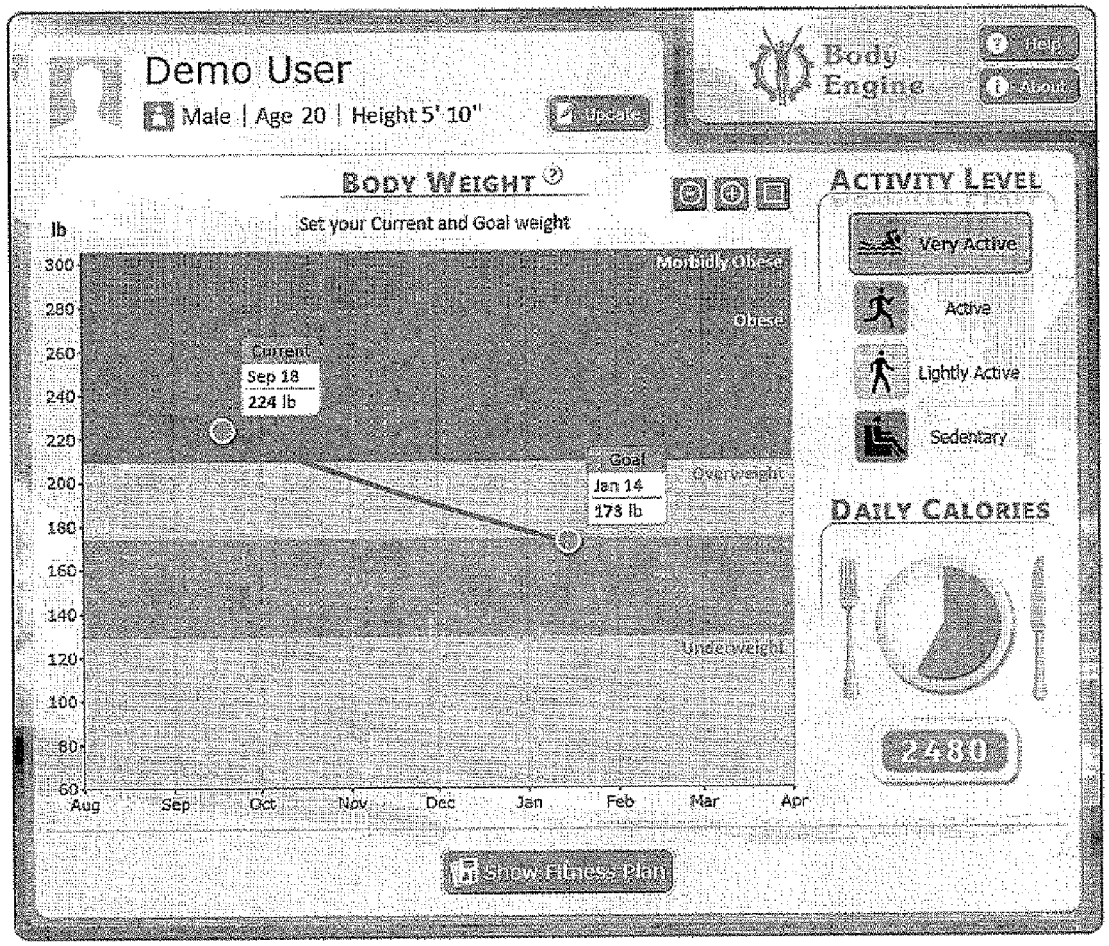
FIG. 8 shows a goal weight slider on a body weight chart, used in an embodiment of the present invention.

Referring to FIG. 8, the body weight chart is displayed with the goal state slider (orange circle with a callout) representing user's desired body weight (173 lb) which the user wants to reach by January 14. Slider's callout displays both the goal date and the goal body weight, and along the time range X-axis is positioned relative to location of the goal date (January 14). Goal state slider is adjustable horizontally (to increase or decrease time it takes to reach the goal weight) or vertically (to decrease or increase the desired goal weight).

Figure 9:
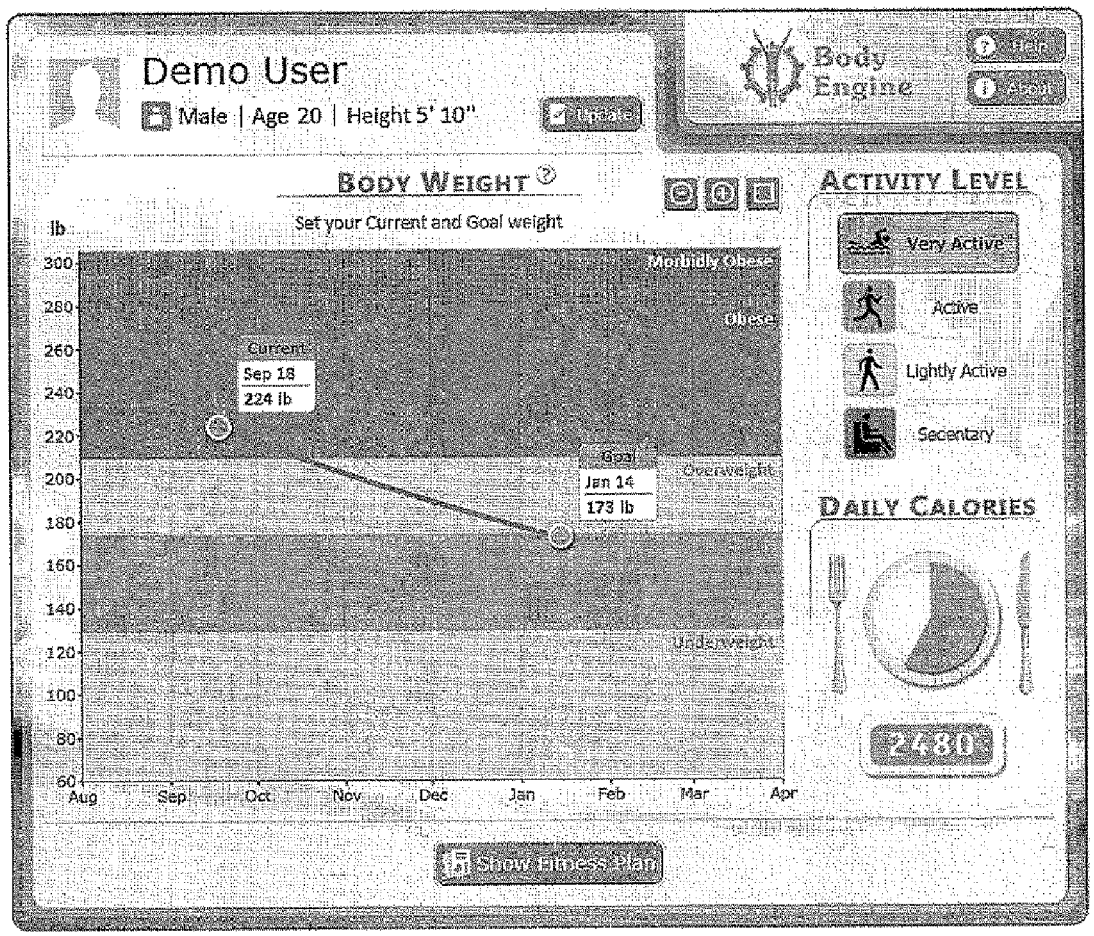
FIG. 9 shows a future progress line on a body weight chart, used in an embodiment of the present invention.

Referring to FIG. 9, the body weight chart is displayed with the future progress line extending from the present date displayed by the chart (September 18) to the goal date (January 14), selected by the user. The future progress line renders in real time as the user adjusts his/her goal weight and goal date by moving goal state slider vertically or horizontally.

Figure 10:
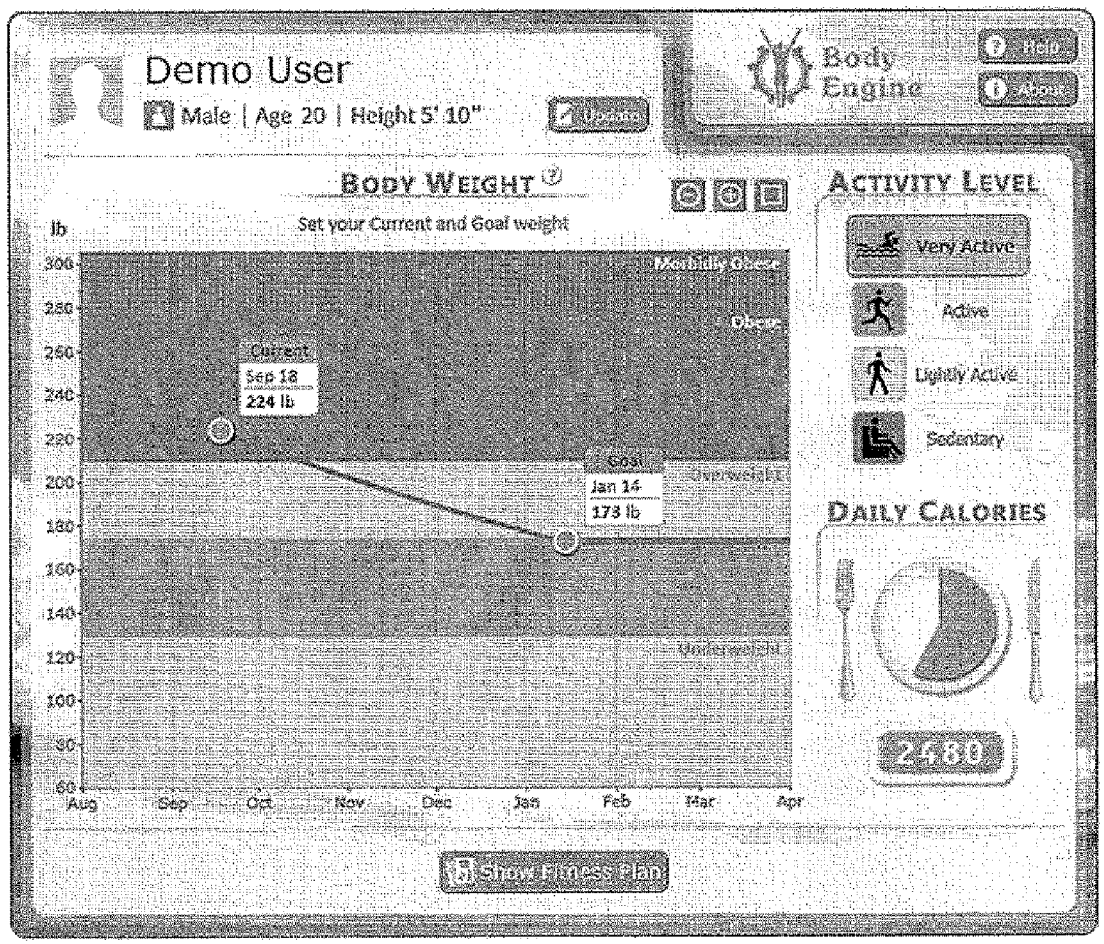
FIG. 10 shows a future progress line past goal date on a body weight chart, used in an embodiment of the present invention.

Referring to FIG. 10, the body weight chart is displayed with the future progress line, which also continues as a horizontal line past the goal date. This representation indicates that upon reaching goal weight the user's weight will remain constant and unchanged from that point onward (which is achieved by increasing Goal EER to the calories intake equal to the EER for the goal weight on goal date).

Figure 11:
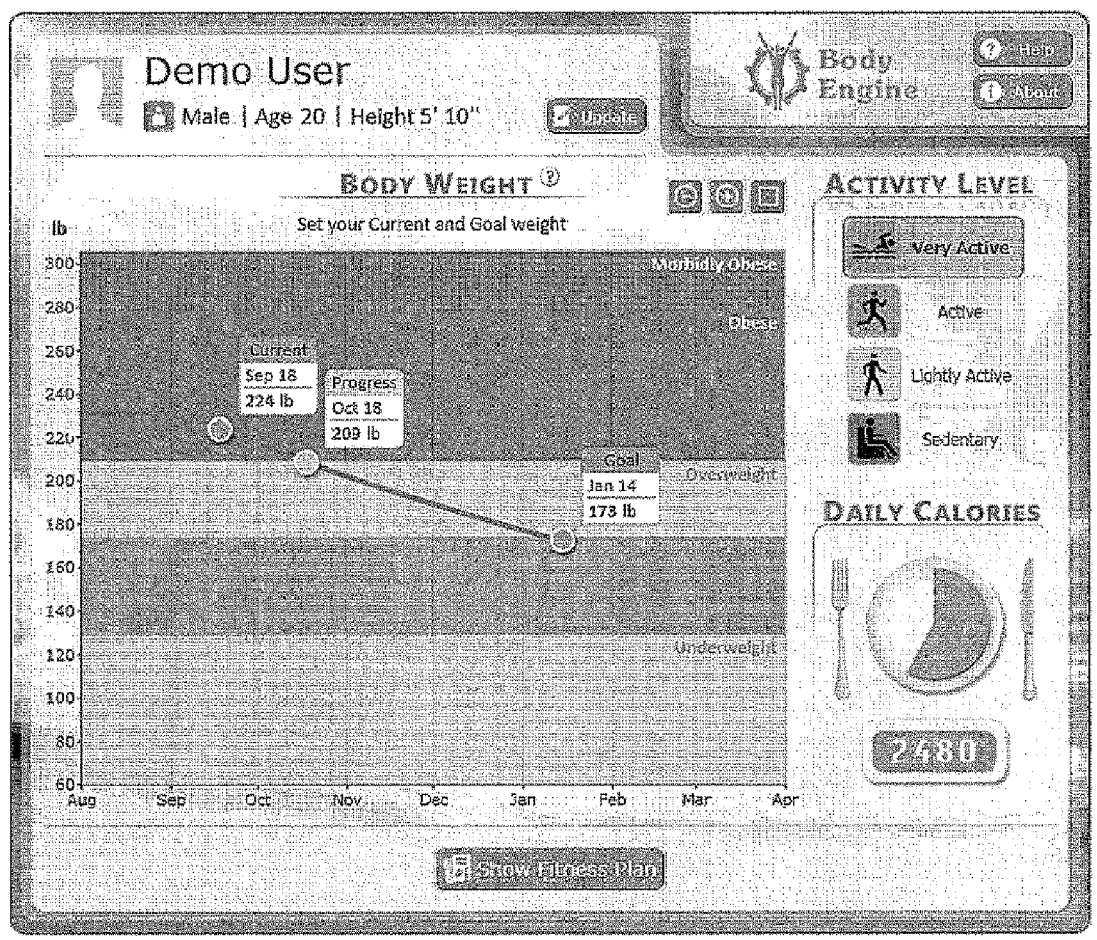
FIG. 11 shows a future progress line intermediate progress state on a body weight chart, used in an embodiment of the present invention.

Referring to FIG. 11, the body weight chart is displayed with the future progress line showing intermediate progress state (gray slider). Each point on the future progress line represents a state of the user's weight on a particular future date within the time range between present date (September 18) and goal date (January 14) as an intersection between the weight axis (Y-axis) and time range axis (X-axis). In the figure, the user mouse clicked on the line at a point where it crosses from Obese BMI color zone to Overweight BMI color zone, so an intermediate state slider appeared with a callout displaying weight (209 lb) and date (October 18) when the user's will reach Overweight weight level while in a process of reaching Goal weight of 173 lb on January 14.

BodyEngine includes a selection zone feature whose purpose is to limit the user's goal selection in the weight or to within safe and realistic ranges.

Figure 12:
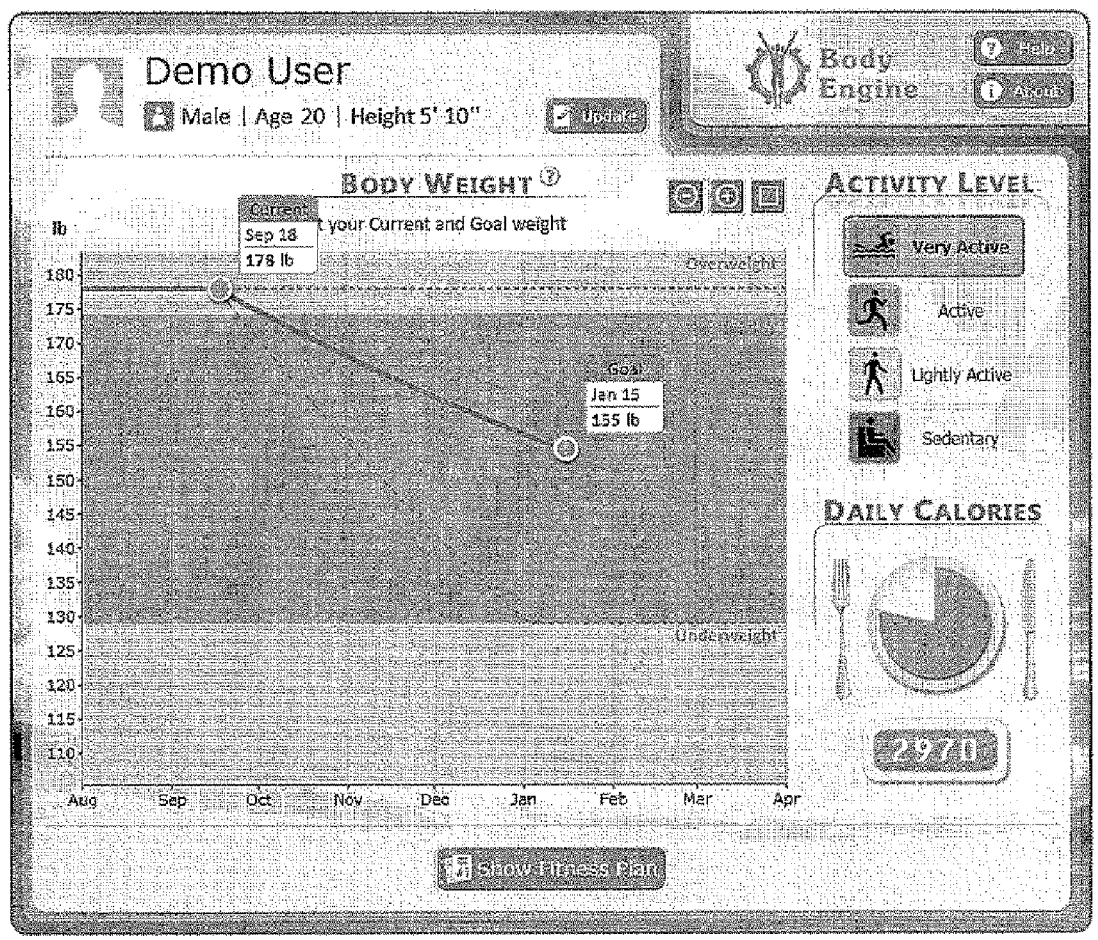
FIG. 12 shows a selection zone for a body weight chart, used in an embodiment of the present invention.

Referring to FIG. 12, the body weight chart is displayed with the selection zone (thin dashed line). Selection zone limits where the goal state slider can be positioned vertically or horizontally, e.g. in the figure the user will not be able to set goal slider to weight greater than 178 lb or less than 129 lb, and won't be able to set goal slider to date before January 2 if the goal weight is set to 129 lb.

Figure 13:
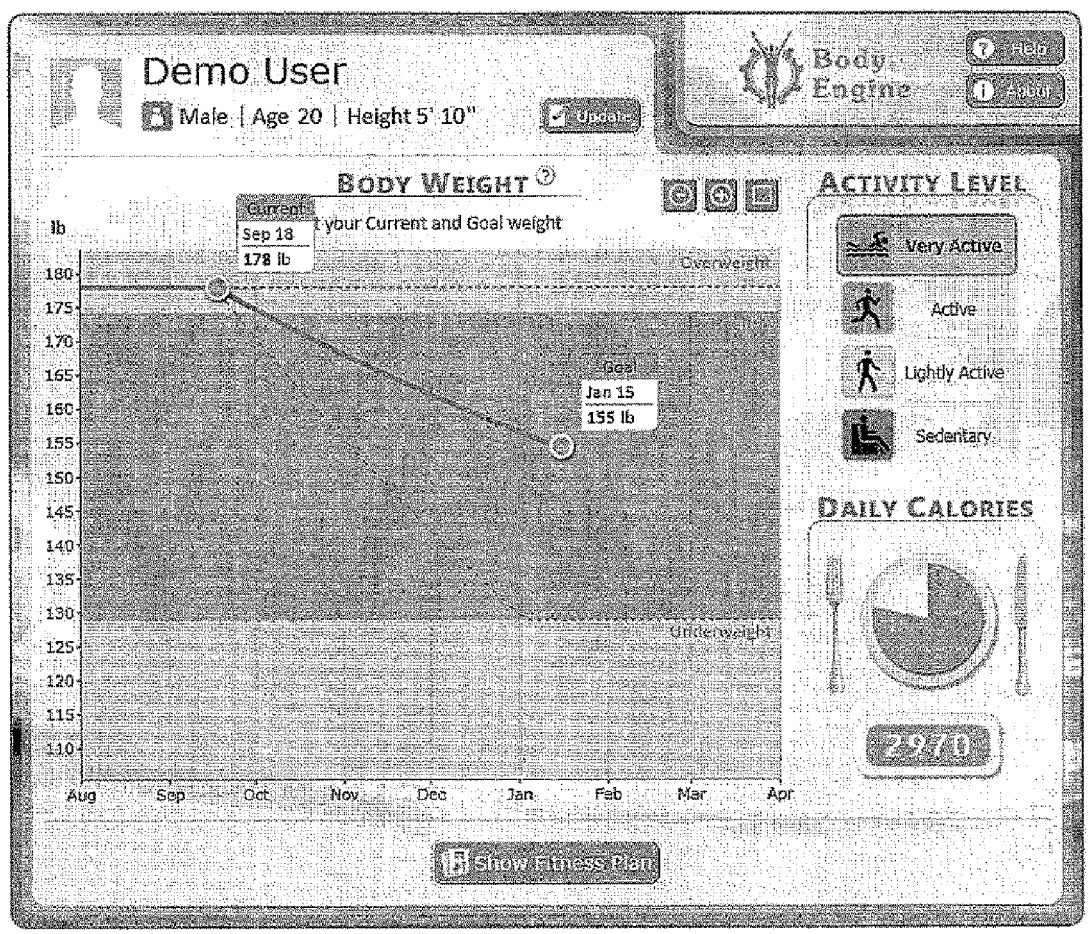
FIG. 13 shows an upper limit selection zone for a body weight chart, used in an embodiment of the present invention.

Referring to FIG. 13, the body weight chart is displayed with the selection zone limiting the goal state slider to 178 lb (current total weight) at the top. This arrangement of current state slider and goal state slider indicates a scenario when user's goal is to maintain his/her current weight (i.e. goal weight equals to the current weight of 178 lb from September 18 to January 12).

Figure 14:
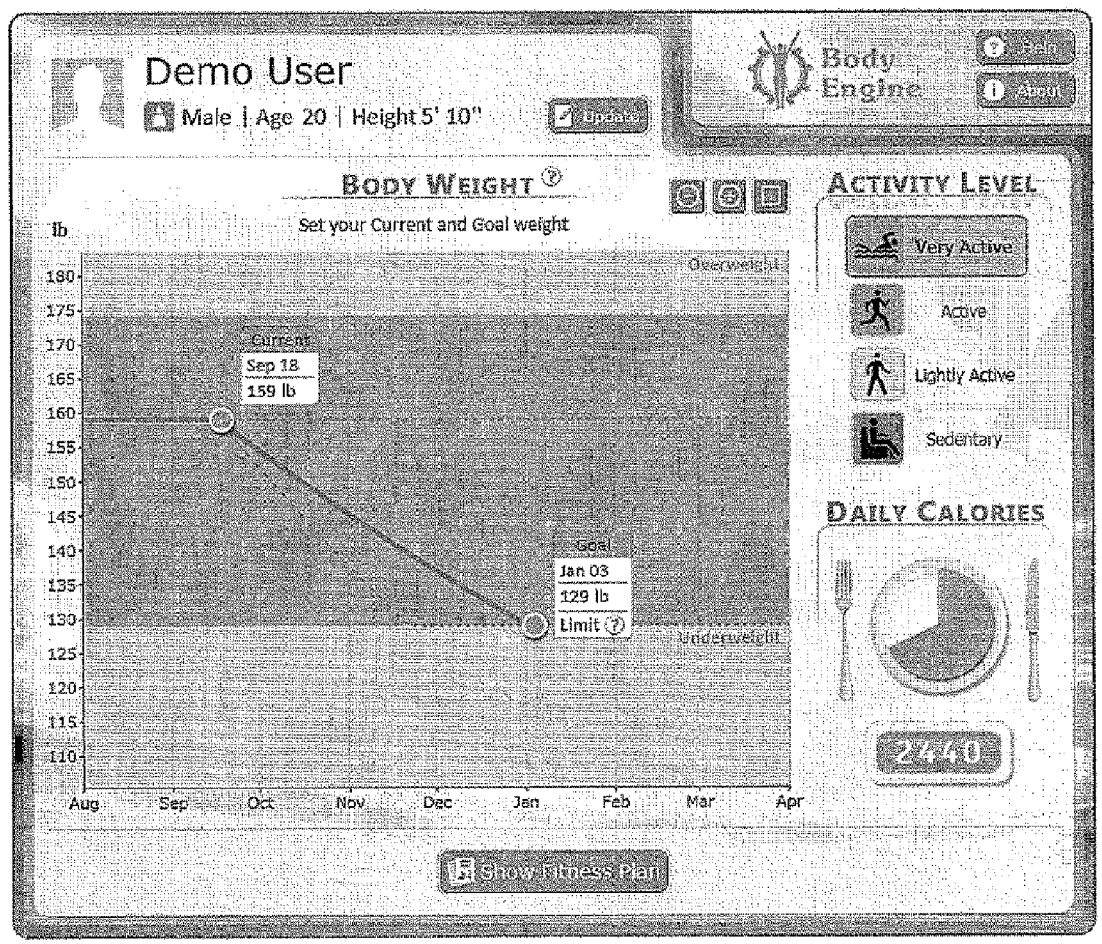
FIG. 14 shows a lower limit selection zone for a body weight chart, used in an embodiment of the present invention.

Referring to FIG. 14, the body weight chart is displayed with the selection zone limiting the goal state slider to 129 lb (weight equivalent to the user's underweight BMI level) at the bottom. This arrangement of current state slider and goal state slider indicates a scenario when user is prevented from setting goal weight to a value considered unhealthy.

Figure 15:
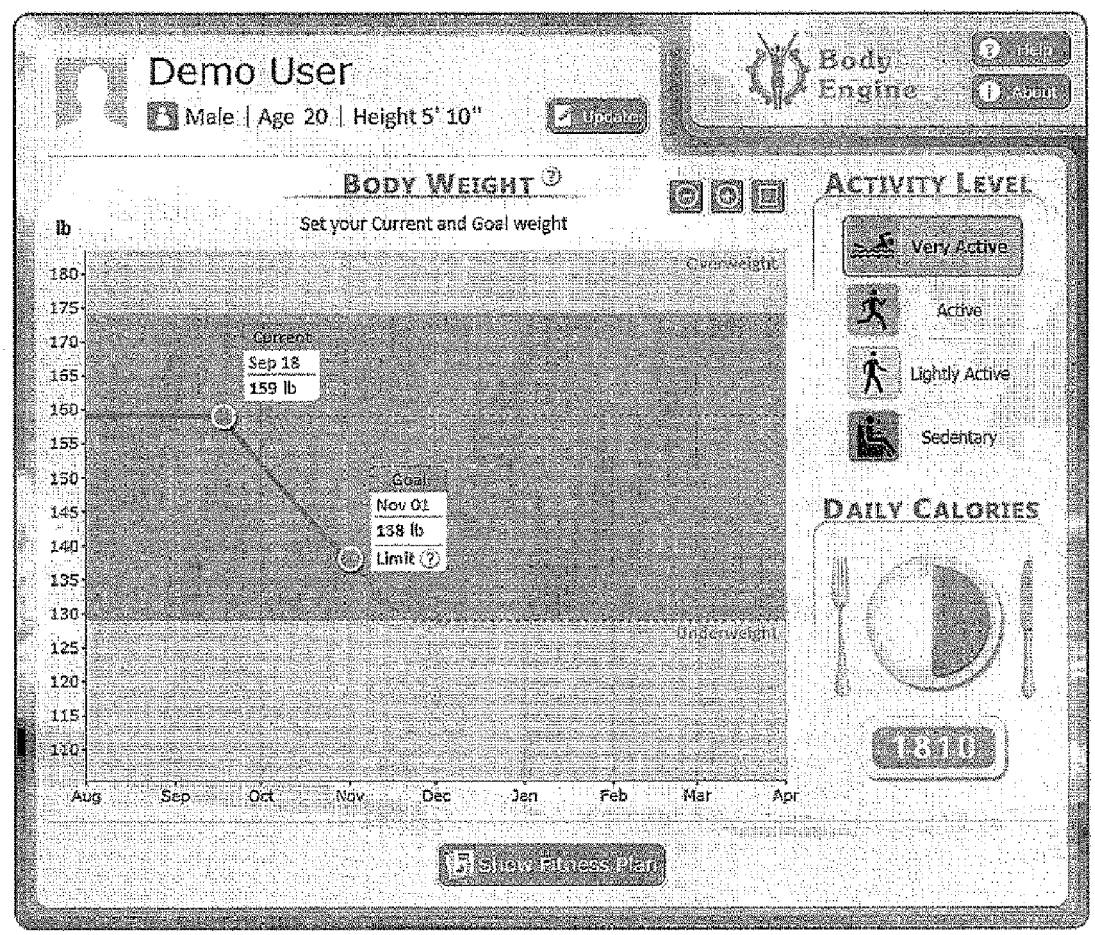
FIG. 15 shows a dynamic limit selection zone for a body weight chart, used in an embodiment of the present invention.

Referring to FIG. 15, the body weight chart is displayed with the selection zone limiting the goal state slider to 138 lb goal weight on goal date of November 1. Both horizontal-left and vertical-down movement of the goal state slider is limited at the intersection point of 138 lb on Y-axis and November 1 on X-axis. This represents a scenario when goal state selection is limited to reasonable and realistic values, i.e. along the X-axis, the earliest date the user will be able to achieve goal weight of 138 lb starting at the current state of 159 lb on September 18, is November 1. In order to set a goal date which is earlier than November 1, the user need to move goal state slider upward to e.g. 140 lb and then to the left. This represent a scenario when goal state selection is limited to safe values, i.e. along the Y-axis, the lowest weight value that the user should be able to reach by November 1 starting from the current state, is 138 lb. This value is calculated by applying BodyEngine dynamic RMR limit algorithm, which is also used to calculate other values along the dynamic limit line between current state and goal state. In order to set a goal weight to value lower than 138 lb, the user need to move goal state slider to the right e.g. to December 1, and then down.

Figure 16:
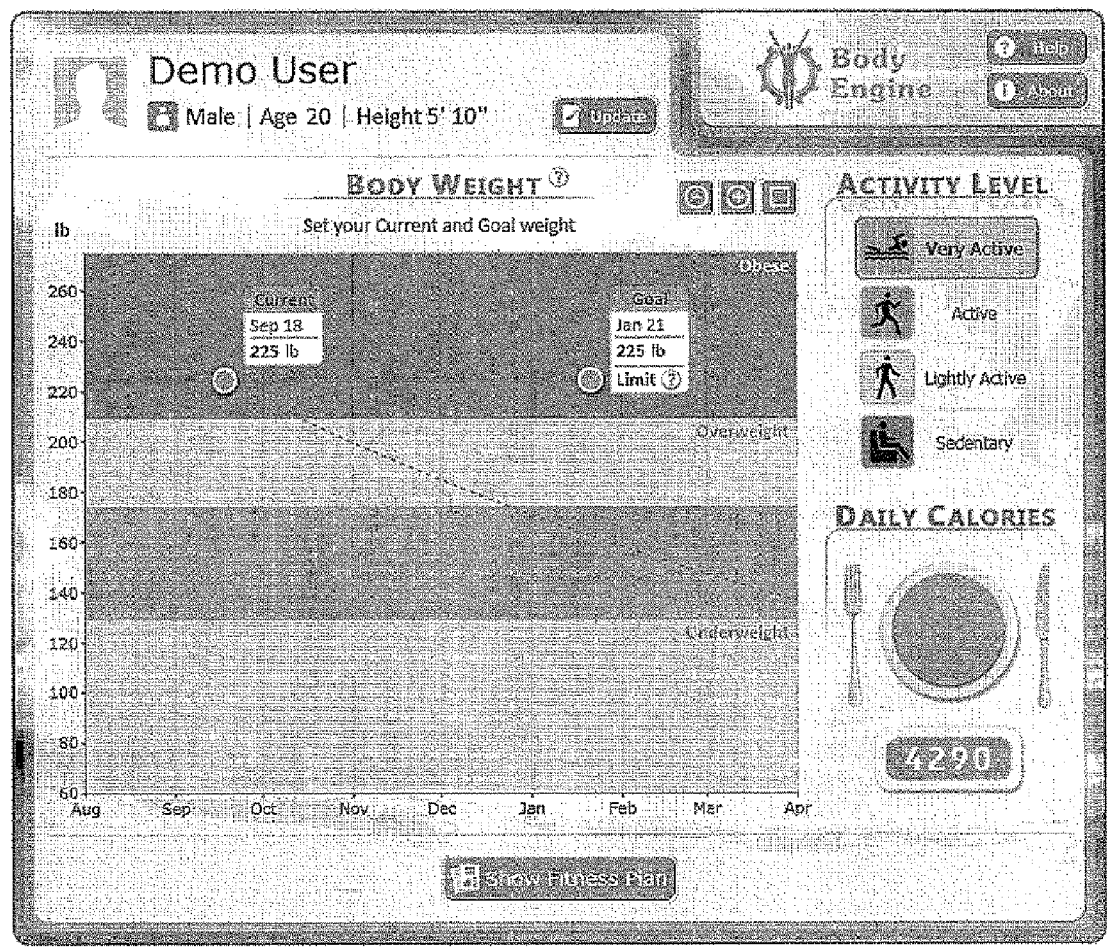
FIG. 16 shows a slider coercion for a body weight chart, used in an embodiment of the present invention.

Referring to FIG. 16, the Body weight chart is displayed with the goal set slider limited (coerced to a certain value) by top line segment of selection zone to the value of 225 lb. When user tries to move goal state slider outside the boundaries of the selection zone, the slider's movement is limited and zone boundaries. However, since selection zone control is dynamic it responds to inputs and changes occurring in other parts of the application, e.g. user changing activity level instead of moving the goal state slider. In situation like this the goal state slider will get automatically forced to the valid value if after selection zone shrinks dynamically the previously valid value of goal state slider is no longer valid. As shown in the figure, the user set current weight to 230 lb, and then set goal state to goal weight of 228 lb on goal date January 21. After that the user changed current weight to 225 lb, which automatically forced goal state slider down to 225 lb so that it doesn't exceed the upper limit of the selection zone, i.e. the slider became coerced.

Figure 17:
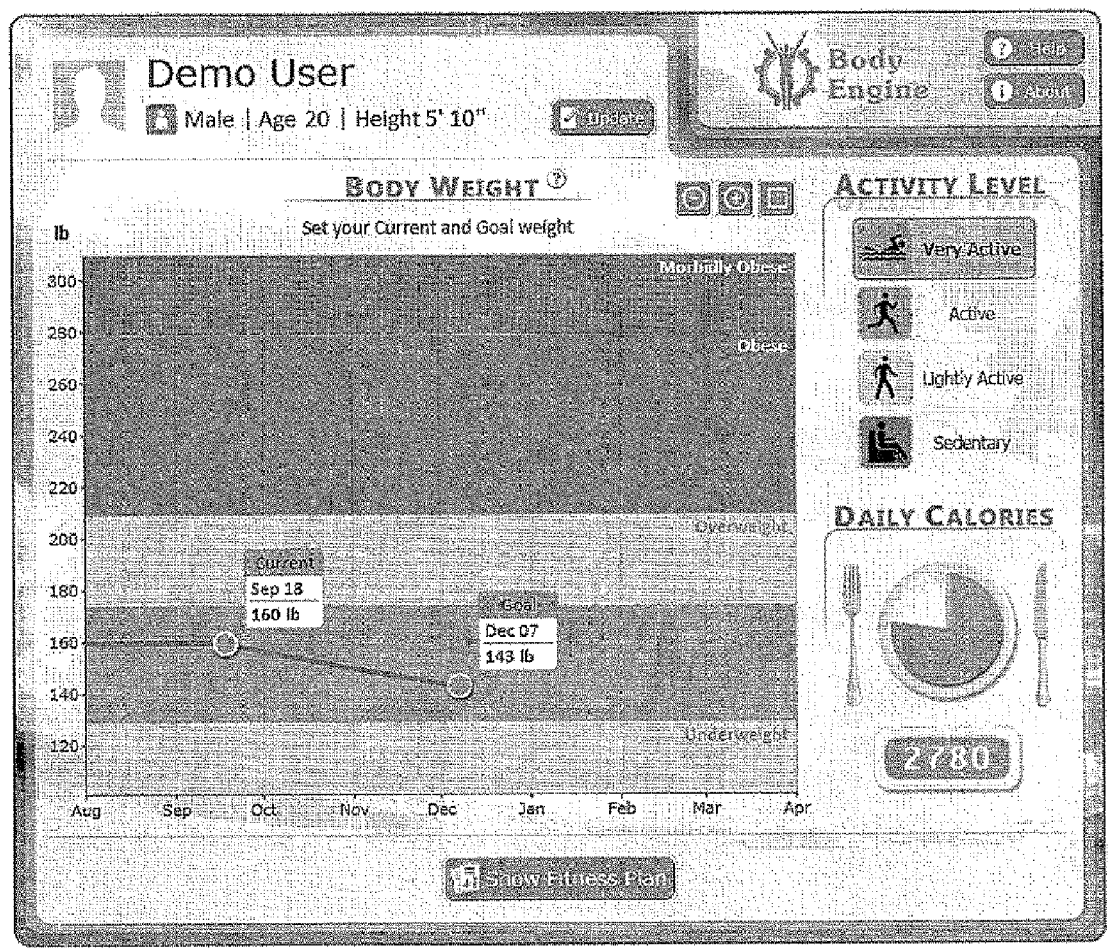
FIG. 17 shows weight level color zones for body weight chart, used in an embodiment of the present invention.

Referring to FIG. 17, the Body weight chart is displayed with the weight level zones in different color rendered in the background. There are five different levels—Underweight, Healthy, Overweight, Obese and Morbidly Obese. Zones are colored accordingly to indicate healthiness or danger. Zone levels indicate weight values equivalent to BMI scores for the user with the current parameters (i.e. the user is a male, 20 y.o., and height 5 feet 10 inches). There is a zone and a corresponding weight value for each BMI classification for this user—e.g. the user is considered Overweight if his BMI score is 25.0 or higher, therefore user's Overweight body weight level is value in pounds (lb) which would yield a BMI score 25.0 or higher, and the smallest such value is 174.25 lb, therefore yellow Overweight zone is rendered starting at that value.

Figure 18:
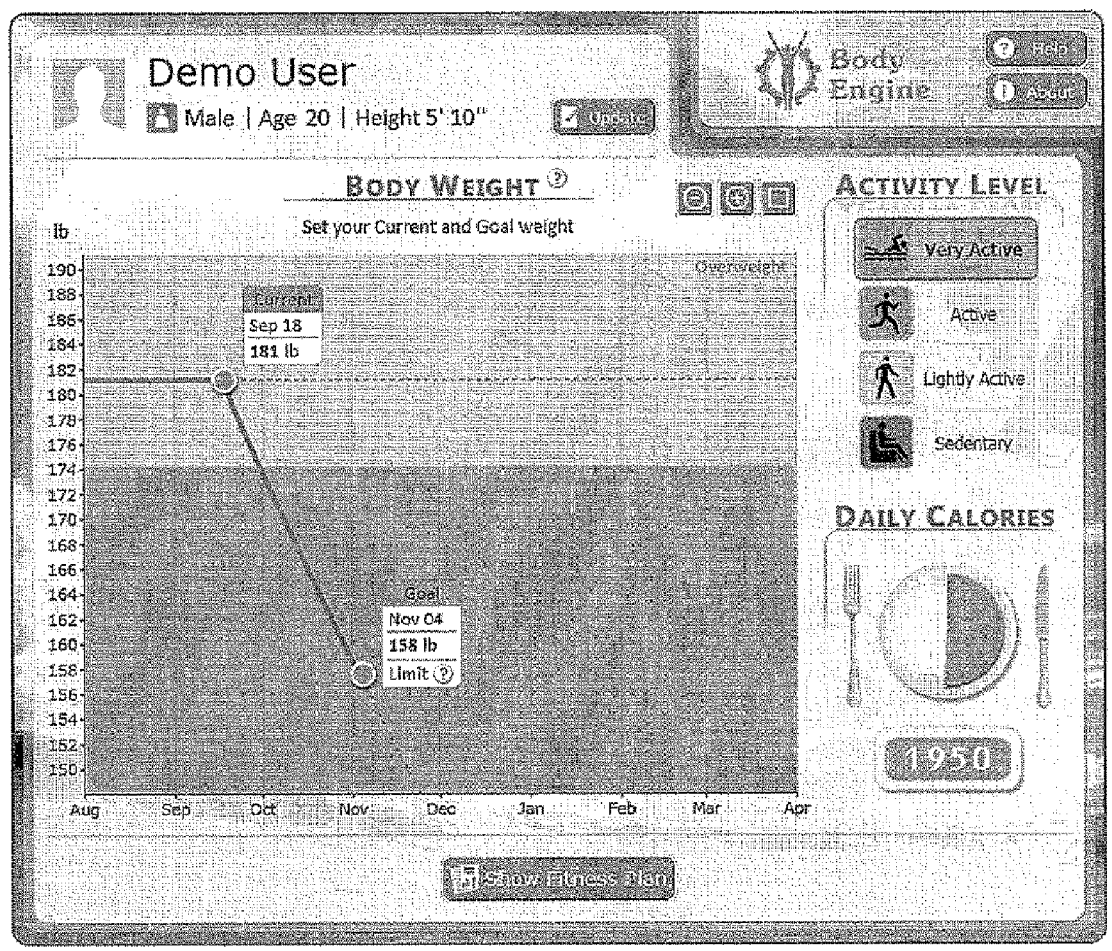
FIG. 18 shows the zoom in/out functionality for the body weight chart, used in an embodiment of the present invention.

Referring to FIG. 18, the Body weight chart is shown at a zoomed in level. Current figure shows chart zoomed in significantly, so that only portion of Overweight and Healthy weight level color zones are shown (compared to FIG. 7 chart and weight level color zones are shown zoomed out almost 100% so that all five zones are visible). The purpose of this functionality is to make it easier for the user to set current and goal state sliders to precisely the values that the user wants, e.g. with a precision to 1 lb. After values are set and the user wants to see a bigger picture, he or she can zoom out as much as necessary.

Zooming is implemented in such fashion that neither the vertical region between current state and goal state sliders, no sliders themselves, are out of the view, e.g. position of sliders determines the greatest zoom-in level attainable on the chart.

Referring to FIG. 19, the Fat Level chart (positioned under the Body Weight chart) is displayed with body fat % of total body weight (Y-axis); time range (X-axis); current fat level slider (orange circle at September 19); goal fat level slider (orange circle at January 1); progress line (dark bold line) with past progress shown to the left of current state slider and future progress shown to the right of the current state slider all the way to the goal state slider; selection zone (thin dashed line); color zones with captions representing Fat Level categories (color background areas and captions on the right side).

Referring to FIG. 20, appearance and functionality of the Fat Level Chart progress line is analogous to appearance and functionality of total Body weight chart progress line described in regarding the progress line, with the only difference that it indicates fat level % instead of weight lb.

Appearance and functionality of Fat Level Chart selection zone is analogous to appearance and functionality of total Body weight chart selection zone described in selection zone section.

Referring to FIG. 20, the Fat Level chart is displayed with the fat % level zones in different color rendered in the background. There are five different levels—Essential, Athletic, Normal, Overfat and Obese. Zones are colored accordingly to indicate healthiness or danger. Fat Level chart color zones are different from body weight chart color zones representing BMI—e.g. on Fat Level chart Normal zone (green) indicates 16-20% body fat for Male and 22-26% body fat for Female, whereas on body weight chart Normal zone indicates total weight lb range (for both Male and Female) which corresponds to a set of weight (lb) values between minimum and maximum Healthy BMI.

Fat level chart zooming functionality is analogous to the zooming functionality of total Body weight chart described in the zooming section.

Figure 21:
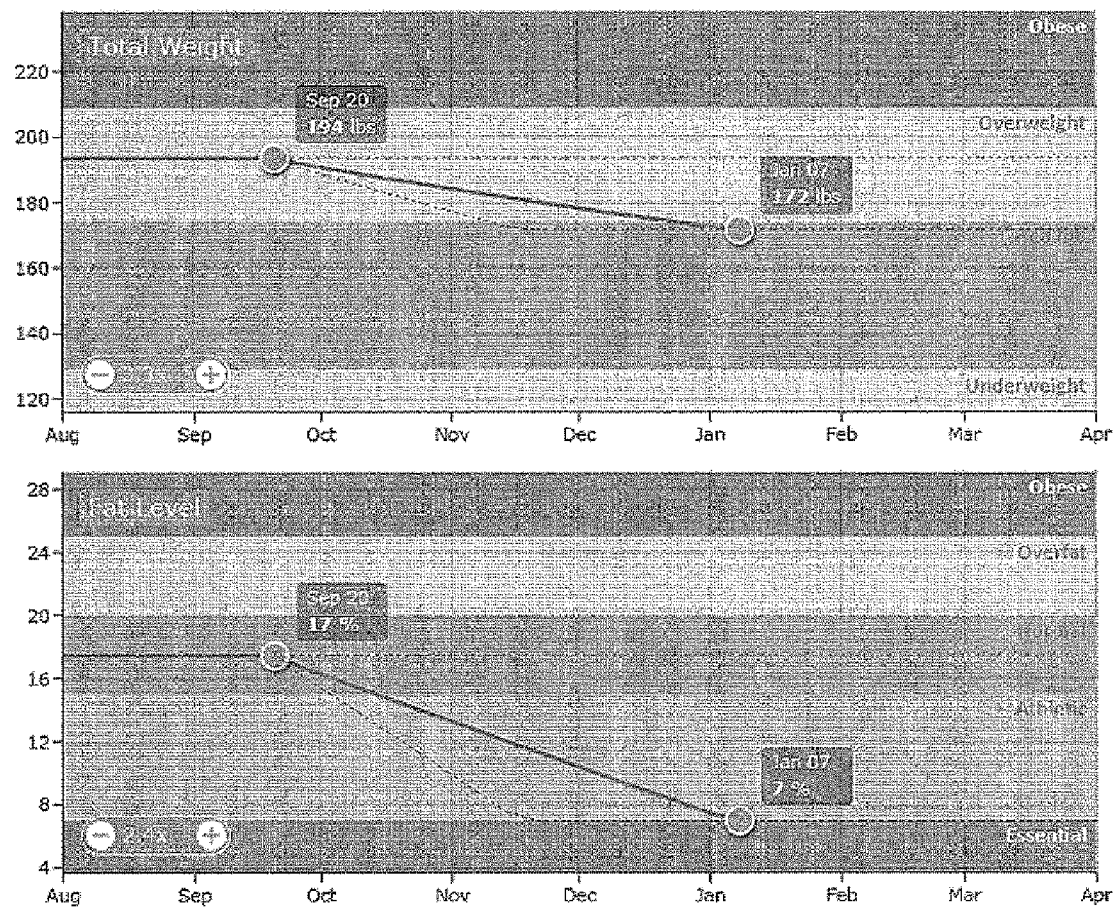
FIG. 21 shows the dual chart view for body weight and fat level charts, used in an embodiment of the present invention.

Referring to FIG. 21, the Body Weight chart and Fat Level chart are shown side by side on the same screen in order to provide the user with the additional level of detail regarding his or her weight and fitness state—e.g. weight and BMI alone do not reveal the full picture about fitness state, because the user's weight may be considered overweight based on BMI number alone, but because fat level is Athletic that's an indication that user's weight consists mostly of FFM (fat-free mass) and the user is heavy not because he or she is overweight but because of a greater amount of FFM compared to someone who is not very muscular and is lighter and thus considered Healthy.

On the figure, according to Body Weight chart color zones (BMI) the user is Overweight, however because body fat level is only 17% as shown on the Fat Level chart, the user is actually Normal.

Figure 22:
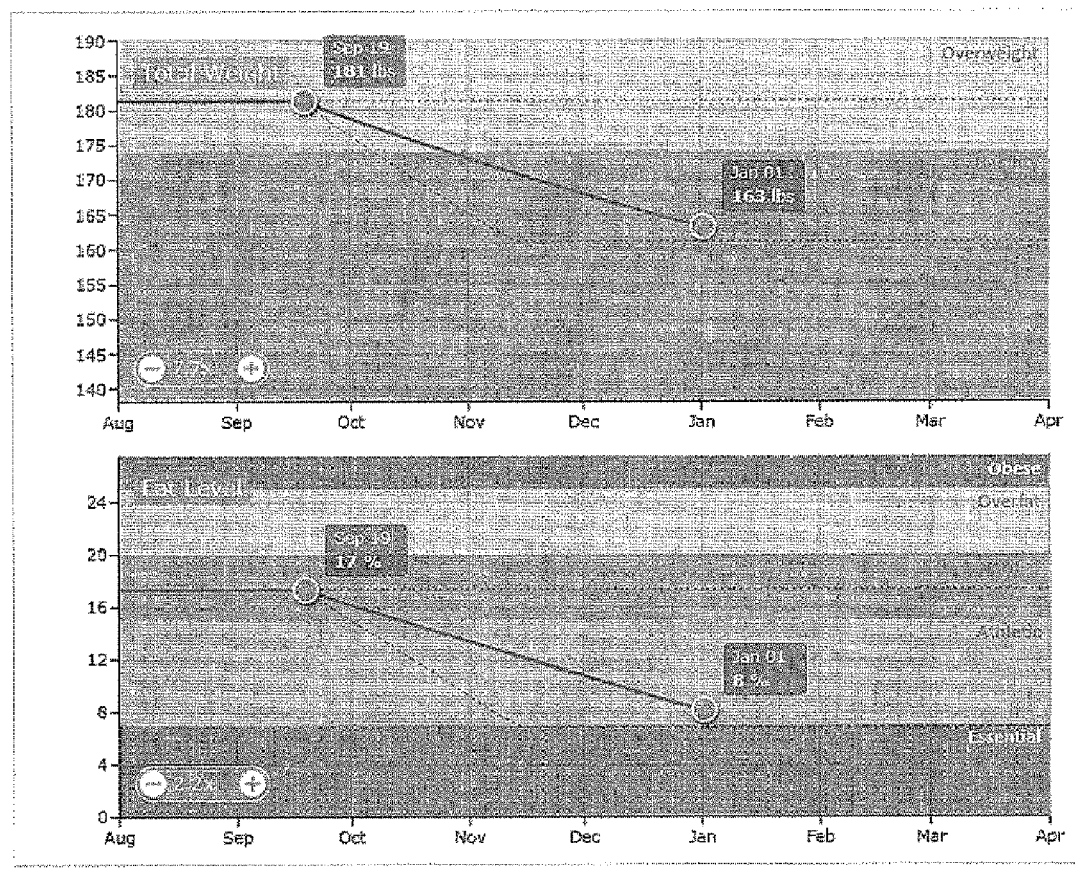
FIG. 22 shows the dual charts view for charts synchronization, used in an embodiment of the present invention.

Referring to FIG. 22, the Body Weight chart and Fat Level chart is shown side by side on the same screen. Main principle behind BodyEngine approach is to reduce weight by retaining FFM (fat-free mass) and losing FM (fat mass). Thus FFM at current fitness state is always equal to FFM at goal fitness state. In order to achieve this, the current fitness state sliders and the goal fitness state sliders on body weight chart and fat level chart remain in sync with each other—e.g. if user is manually adjusting current total weight the current fat level slider adjusts automatically because FFM stays the same and the weight change is reflected in lower (or higher) body fat %.

Additionally, goal fitness state sliders synchronize horizontally along the time range (X-axis), to emphasize that they represent the same fitness state on the same date at some point in the future. Synchronization of the charts does not depend on the zoom level of the charts and both charts can be zoomed in or zoomed out independently.

Figure 23:
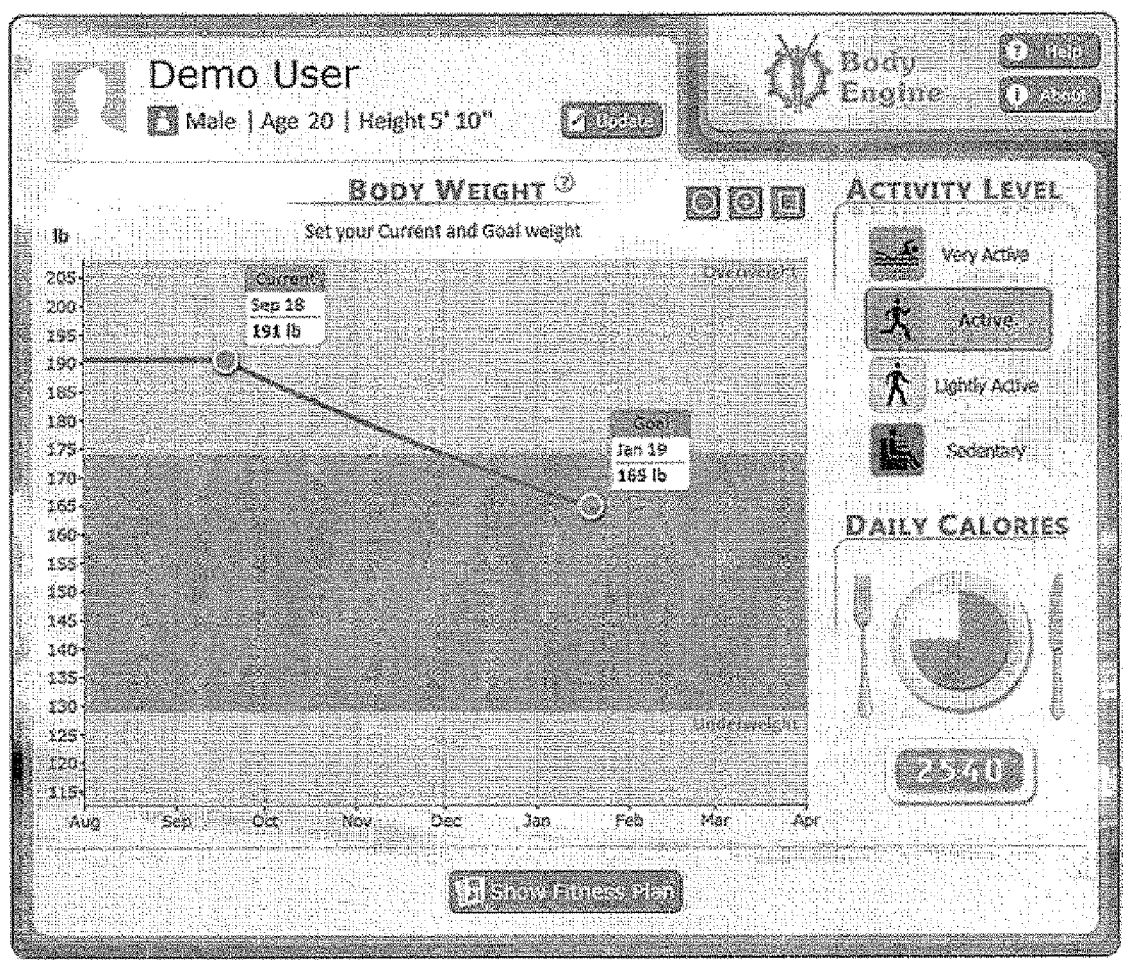
FIG. 23 shows the overall daily plate, used in an embodiment of the present invention.

Referring to FIG. 23, the Daily Plate display includes a pie chart representing combined daily meals (large orange circle with 2π/3 rad filled over an image of plate) and the required daily calories intake number (white number inside orange rectangle). In this figure, daily plate indicates that the user should be consuming 2540 Calories daily to reach the goal weight of 165 lb, and that this calories number is about 75% (hence only 2π/3 of the pie chart circle is filled) of Calories required to maintain current weight of 191 lb unchanged.

Referring to FIG. 24, the Daily Plate display showing a pie chart with ~3.9 rad filled, indicating that the user's goal daily calories intake is 63% (e.g. deficit of 37%) of what is required to maintain his/her current weight constant. Indeed, the daily calories intake required to reach goal weight of 16 lb (2150 Calories) is ~37% less than 3390 Calories required to maintain current weight of 191 lb.

Figure 25:
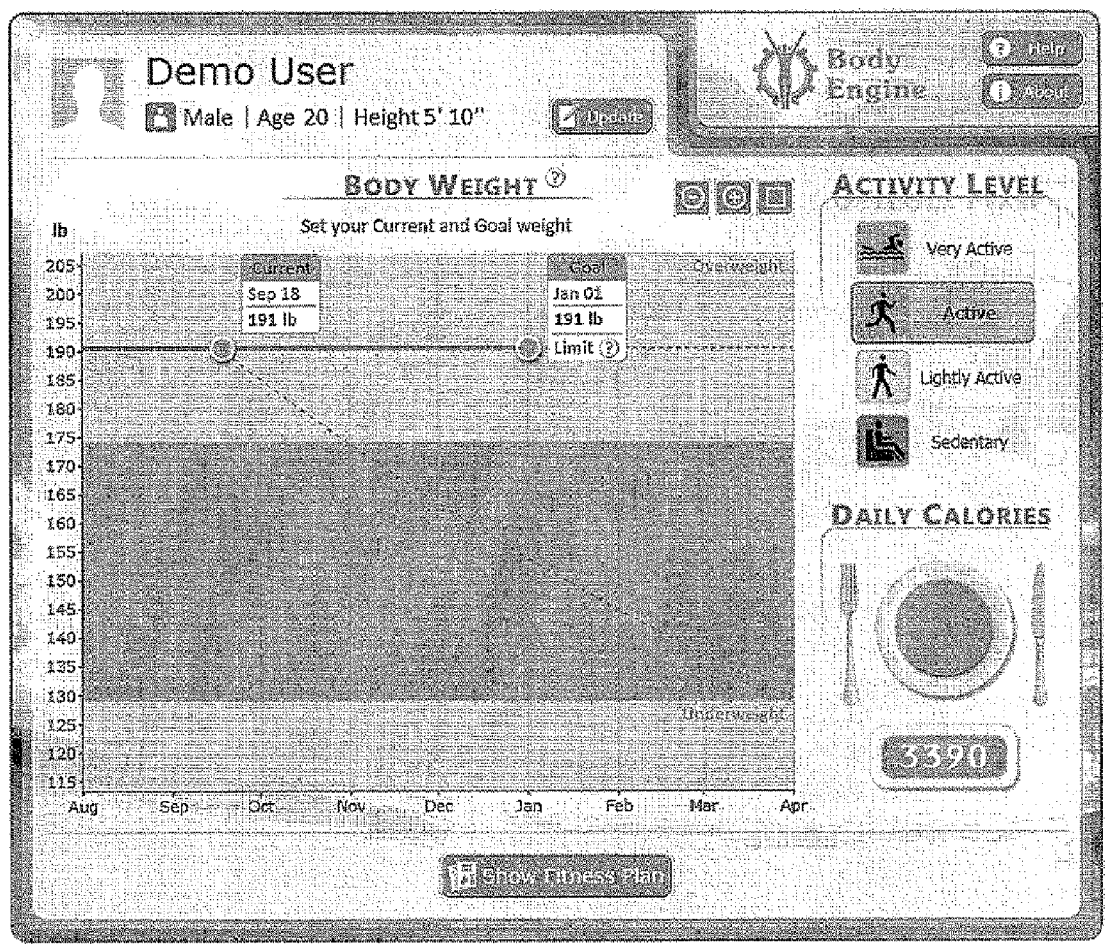
FIG. 25 shows the full pie chart for the daily plate, used in an embodiment of the present invention.

Referring to FIG. 25, the Daily Plate display shows a pie chart 100% filled and with goal weight slider set to the same weight value as the current weight slider, indicating that the user's goal is to maintain current weight of 191 lb constant at least until January 1, and that daily calories intake is the same as current weight maintenance calories 3390 Calories per day.

Figure 26:
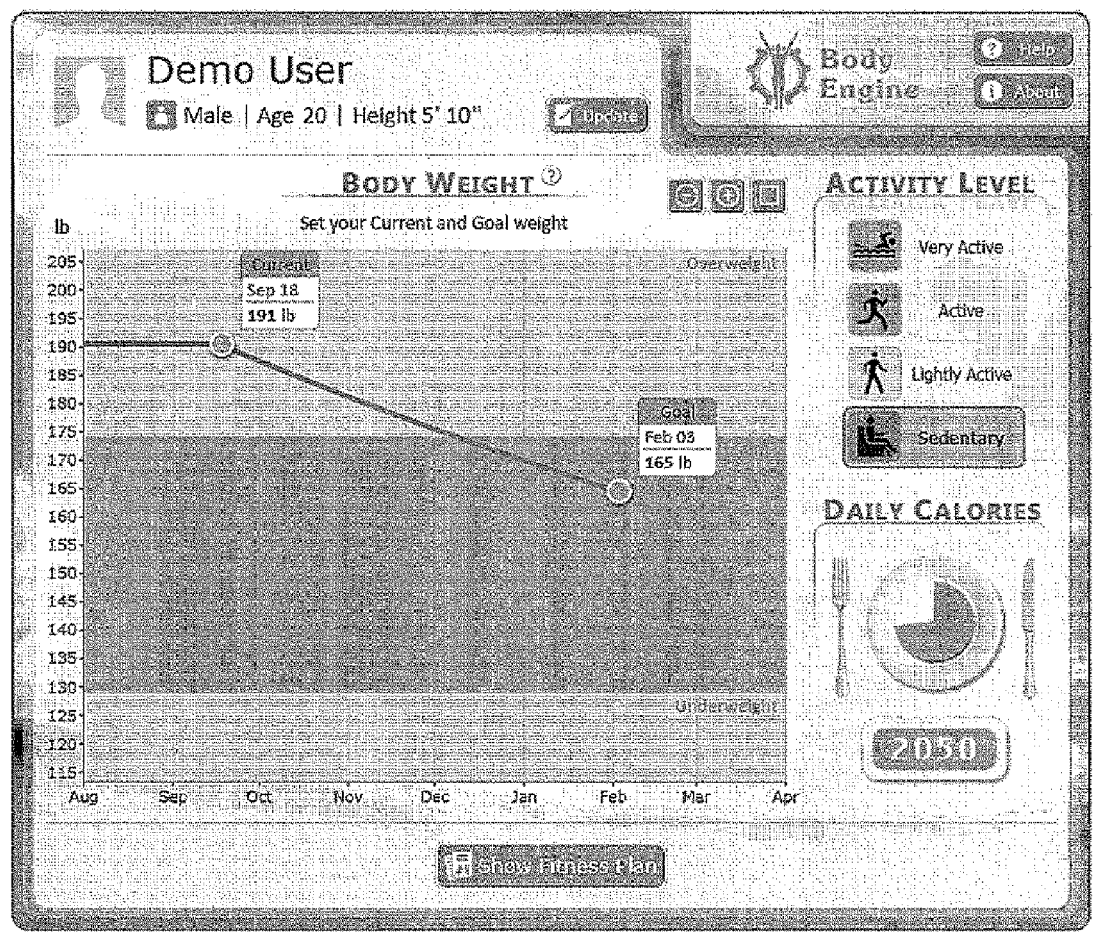
FIG. 26 shows the sedentary pie chart for the daily plate, used in an embodiment of the present invention.

Referring to FIG. 26, the Daily Plate is displayed with a pie chart showing percent of goal calories intake from current weight maintenance calories intake at Sedentary activity level (about 75% of maintenance). If activity is changed, this % may change even if current and goal fitness states remain unchanged. This is because calories intakes are calculated using EER formula which includes activity level, so EER values for the same body weights would be different at different activity levels, therefore their proportion may also be different.

The radius of the pie chart represents percent of goal calories intake at selected activity (sedentary in this case) from goal calories intake at Very Active activity since that is maximum attainable calories intake for the current and goal fitness states.

Figure 27:
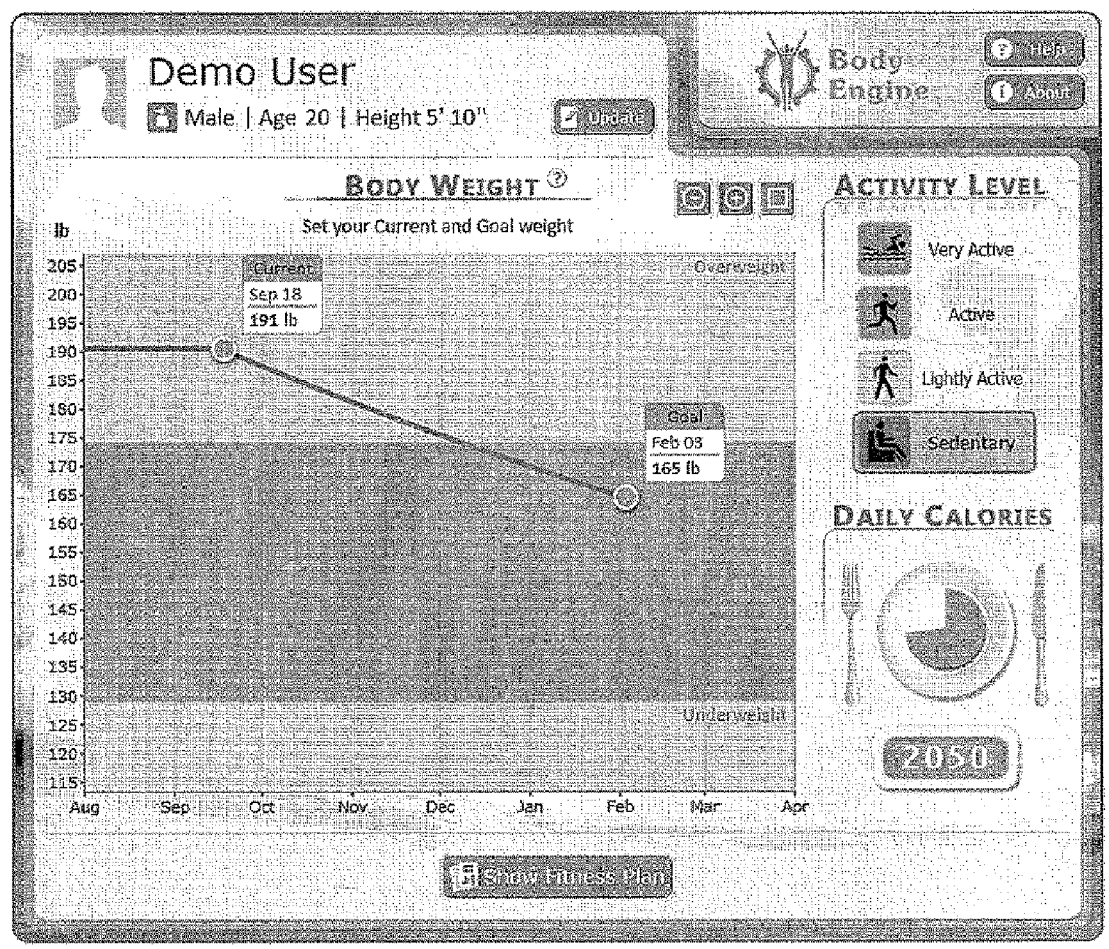
FIG. 27 shows the very active pie chart for the daily plate, used in an embodiment of the present invention.

Referring to FIG. 27, the pie chart shows scenario similar to FIG. 26, with a difference that radius of pie chart is at max (100%) because Very Active activity level is selected. Also since activity has changed (from Sedentary to Very Active) compared to previous example and so did current maintenance calories intake and goal calories intake, the proportion of between these two intakes is now different (hence circle is ~80% complete instead of 75%).

Figure 28:
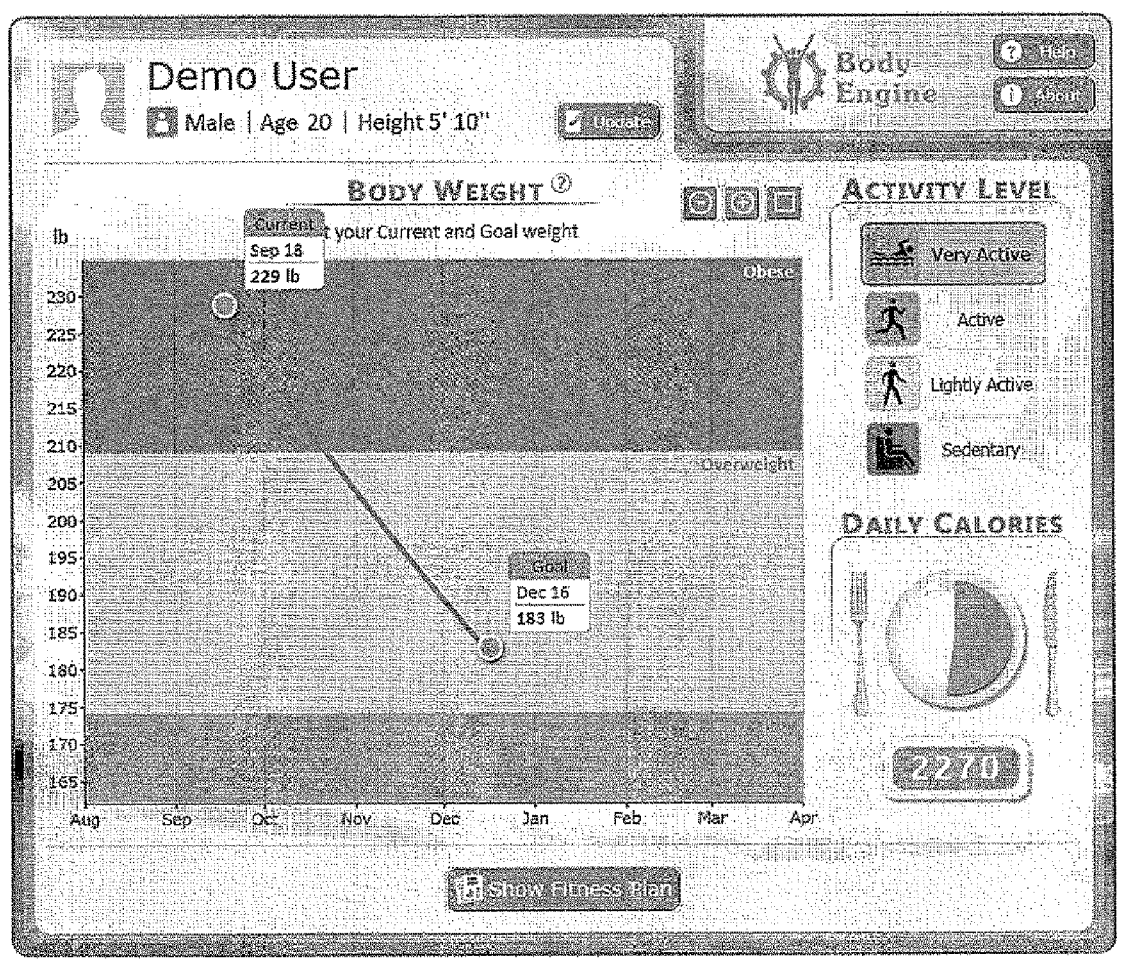
FIG. 28 shows the goal calories intake for the daily plate, used in an embodiment of the present invention.

Referring to FIG. 28, the Daily Plate display shows goal calories intake of 2240 calories per day, required for the user to be consumed in order to reduce current body weight of 229 lb down to 183 lb by December 16, while maintaining Very Active activity level. Pie chart shows that this calories intake is almost 50% of what the user need to consume every day if he or she wanted to maintain current weight of 229 lb instead of reducing it (i.e. to lose weight per goal selection would require cutting current daily calories intake almost in half).

Advantageous features of BodyEngine over other physical fitness software are discussed herein below. Some of the features apply to non-fitness software as well. The user interface is integrated, dynamic, interactive, complete, user-Friendly, intuitive, and requires minimal interaction. The Interactive fitness console is made up of dynamic controls that remain in synch with each other to provide a clear view of the user's current state, goal fitness state, and how to reach it. The application uses an interactive chart-based user interface (UI) for personal fitness tracking The application uses chart-based UI showing past fitness progress, current fitness state, and future fitness goals. The user's interaction is visual and the response is immediate. The user is not asked to fill out forms or press buttons to calculate results and can accomplish most tasks by just using a pointer (mouse, finger, etc.). The interface requires minimal interaction from the user. No need to type data values and step through wizards. Everything is integrated into a single UI. Setting values on interactive and dynamically computed chart which is immediately updated, instead of static pre-computed chart that only gets updated after all values have been entered.

The application uses multiple dimensions of fitness metrics integrated into a chart-based interface with movable sliders, lines, color zones, selection zones, etc.

The application uses movable chart sliders used to specify the goal date, the total weight, fat level, lean weight, fat weight; calories to be consumed, rate/intensity of dieting, activity level.

The application represents Weight or Fat Level progress as an interactive line with past, current, progress, and final goal fitness states. The user can redraw the line by drag and drop functionality.

The application uses a UI showing interactive charts with past, current, and goal fitness states: total weight, lean weight, fat weight, fat level, activity level, caloric intake and goal date that is dynamically updated based on the following user inputs: Current Age, Gender, and Height; Current and Goal Weight, Lean Weight, Fat Weight, Fat Level; Current and Goal Activity Level (Activity Level can be: Very Active, Active, Lightly Active, Sedentary); Current and Goal Caloric Intake; and Goal Date.

The user can choose from the most aggressive to the least aggressive rate at which to reduce his fat weight while maintaining his original lean weight. The user can adjust the intensity of a combination of activity level, calories, and time, to reach a specified goal weight and fat level.

The application uses a visual representation of a user's Body Mass Index (BMI) as horizontally stacked colored zones representing underweight, normal weight, overweight and obese levels on a chart showing the user's past, current, and goal BMI in relation to weight and time., while all currently available alternative fitness applications omit the time factor from the BMI representation and only focus on either present or goal state.

The application uses a visual representation of Fat Level limits as horizontally stacked colored zones representing underweight, essential, athletic, healthy, overweight and obese fat level on a chart in relation to weight and time.

The present invention uses safe and realistic goals that are enforced through the chart selection zone which enforces safe and accurate goals by limiting the user's goal selection zone for weight and fat level. An algorithm is used to determine the safe and unsafe boundaries for a person's weight at any time from the current date to the future. The algorithm determines the scientifically provable safe boundaries and unsafe boundaries for a person's weight at any time from the current date to the future.

The UI limits the user to set the goal fitness state within safe weight loss or weight gain zones that are dynamically updated when the user adjusts the input. The UI limits the user's interaction within a specific area of the chart. The UI shows boundaries around a specific area of the chart. The UI uses Dynamic boundary lines around one or more specific areas of a time and weight/fat level/fat weight/lean weight based charts.

Figure 29:
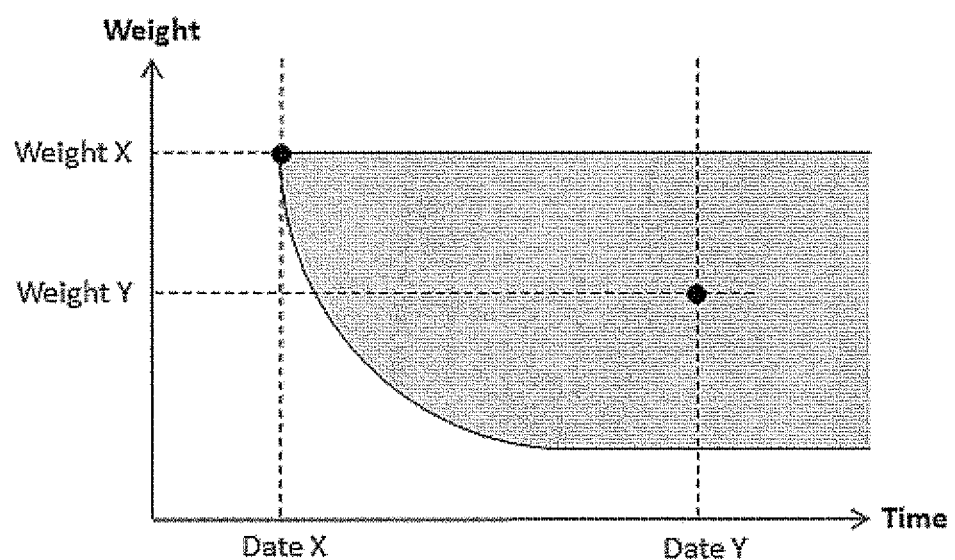
FIG. 29 shows the selection zone, used in an embodiment of the present invention.

Referring to FIG. 29, selection zone boundaries are determined in such a way that for any current weight (or fat level) on the current date, i.e. current state point (Date X, Weight X), any point that lies within the selection zone is a goal state point (Date Y, Weight Y) such that Date Y>=Date X, and Weight Y<=Weight X, and that a single calories intake number can be determined which if consumed by the user on daily basis from Date X to Date Y will result in his/her current state advance to the goal state while other parameters (gender, age, height, activity level) are held constant.

The present invention computes and permits visualization of the calories. The present invention uses an efficient algorithm that leverages fitness science to calculate the constant daily calories to consume in order to reach a specified weight by a specified time period. The fact that the calories are constant is an advantage because it makes it easy for the user to remember and implement in his routine. The fact that it is efficient, allows the application to compute the calories number in real-time in response to user-interaction.

The daily calories plate provides a visual representation of the daily calories needed and the proportion of goal calories vs. current weight maintenance calories. The present invention uses algorithms to make the plate pie-chart grow dynamically in response to selected activity and to fill up based on daily needed calories.

In the present invention, the weight and fat level is calculated over time through use of an algorithm to compute the user's weight and fat level progression over time. A synchronization mechanism between the user's total body weight parameter and fat level parameter ensures that gradual weight loss occurs due to reduction of FM (fat mass) while FFM (fat-free mass) remains unchanged between the current date and the goal date selected by the user (i.e. lean weight preservation). This is also enforced visually on the application GUI by coercing fitness state sliders on weight and fat level charts.

There is also an algorithm to optimize rendering performance (minimize lag) of chart in real-time in response to user's mouse interaction and his computer load. Under heavy load, the application will render fewer frames and under less load it will render more frames without reducing the visual appearance.

There are optimal and dynamic chart zooming algorithms, which ensure that the current and goal sliders are never out of view. The zooming mechanism constructs the view region with edges above the current fitness state slider and below the goal fitness state sliders (since goal fitness state slider is always either on the same level as current fitness state slider or below to indicate weight loss). Dynamic zooming invoked upon slider reaching the edge of the visible view region result in one-directional zoom out (upward for current fitness state slider and downward for goal fitness state slider), thus always presenting the user with either a full or nearly full view of stacked color zones (for the entire supported weight range), or just the region that's relative to the user's current and desired goal state for maximum accuracy while setting sliders.

The present invention dynamically tracks a person's fitness progress and guides him/her to reach his/her desired goal weight and fat level by continuously adjusting the progress path to reach a desired goal by a desired time. To achieve this, upon launching the application the user's current weight is updated automatically based on previously selected states (i.e. current weight is set to previously estimated weight) while allowing the user to override it with the actual weight (if it's different) at any time. This may also be done for other physical parameters, such as a users fat level.

The present invention detects when the user deviates from the originally set progress path and recalculates a new progress path by which the user can still reach the same goal weight and fat level by the original goal date.

The present invention detects when the user deviates from a predetermined progress path into an unattainable and/or unsafe progress path; automatically recalculates an attainable and safe progress path that is closest to the original progress path.

The present invention automatically adjusts the progress path by which the user can reach a specified goal weight and fat level by a specific time when it detects changes to total weight, lean weight, fat level, age, height and activity level.

The present invention continuously provides a person with the exact (scientific) constant number of calories to consume every day from the current date until the goal date that will result in the person reaching his/her predetermined goal fitness state (goal weight and goal fat level).

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A physical health application accessible via a computer network comprising:
   a processor;
   a dynamic user interface comprising an interactive chart;
   wherein the interactive chart displays at least one physical parameter selected from a group consisting of total weight, lean weight, fat level, age, gender, and activity level, over time and said at least one physical parameter is adjustable using said dynamic user interface;
   wherein the interactive chart is adapted to be adjusted to set a physical progress goal weight and a physical goal date;
   wherein the interactive chart is adapted to display a dynamic selection zone that defines possible physical progress goal weight and date selections based on the at least one physical parameter, allows a user to select a physical progress goal weight and date within the dynamic selection zone, automatically updates the possible physical progress goal weight and date selections in response to said adjustment of the at least one said physical parameter, and prevents the user from setting an unhealthy or unattainable physical progress goal weight and date.

2. The application of claim 1, wherein the dynamic user interface further comprises an activity level setting interface, wherein adjusting an activity level further adjusts the interactive chart.

3. The application of claim 1, wherein the dynamic user interface further comprises a daily calorie intake display, wherein adjusting the interactive chart further adjusts the daily calorie intake.

4. The application of claim 1, wherein the interactive chart displays a first progress path based upon the physical progress goal and a physical progress goal date.

5. The application of claim 4, further comprising means for detecting a deviation from the first progress path and means for calculating a second progress path to reach the set physical progress goal by the physical progress goal date.

6. The application of claim 5, wherein said means for detecting a deviation from the first progress path calculates a second progress path closest to the first progress path when said first progress path deviates into an unattainable and/or unsafe progress path.

7. The application of claim 6, further comprising means for adjusting the first progress path by detecting changes to total weight, lean weight, fat level, age, height and activity level.

8. The application of claim 1, further comprising means for displaying goals on a social networking site.

9. The application of claim 1, wherein a boundary of the selection zone is determined by a resting metabolic rate.

10. The application of claim 1, further comprising means for dynamically zooming.

11. The application of claim 1, further comprising means for updating at least one physical progress goal if said physical progress goal falls outside of an updated selection zone.

12. The application of claim 11, wherein said means for updating labels an updated physical progress goal to indicate that said physical progress goal has been updated.

13. A method for tracking physical health via a computer network application comprising:
displaying at least one physical parameter selected from a group consisting of total weight, lean weight, fat level, age, height, gender and activity level, over time on a dynamic user interface comprising an interactive chart;
said at least one parameter is adjustable using said dynamic user interface adjusting a physical parameter on the interactive chart; and
displaying a dynamic selection zone on the interactive chart, wherein the dynamic selection zone defines possible physical progress goal weight and date selections, automatically updates the possible physical progress goal weight and date selections in response to adjustment of at least one said physical parameter, and prevents a user from setting an unhealthy of unattainable physical progress goal weight and date; and
setting the physical progress goal weight and date by making a selection from within the dynamic selection zone.

14. The method of claim 13, wherein the dynamic user interface further comprises an activity level setting interface, and wherein adjusting an activity level via the activity level setting interface further adjusts the interactive chart.

15. The method of claim 13, wherein the dynamic user interface further comprises a daily calorie intake display, and wherein adjusting the interactive chart further adjusts the daily calorie intake display.

16. The method of claim 13, wherein the interactive chart displays a first progress path based upon the physical progress goal and a physical progress goal date.

17. The method of claim 16, further comprising steps of detecting deviation from the first progress path and calculating a second progress path to reach the set physical progress goal by the physical progress goal date.

18. The method of claim 17, wherein a second progress path closest to the first progress path is calculated when said first progress path deviates into an unattainable and/or unsafe progress path.

19. The method of claim 18, further comprising adjusting the first progress path based on changes to total weight, lean weight, fat level, age, height and activity level.

20. The method of claim 13, further comprising displaying goals on a social networking site.

21. The method of claim 13, wherein a boundary of the selection zone is determined by a resting metabolic rate.

22. The method of claim 13, further comprising a step of updating at least one physical progress goal if said physical progress goal falls outside of an updated selection zone.

23. The method of claim 22, further comprising a step of labelling an updated physical progress goal to indicate that said physical progress goal has been updated.

24. The method of claim 23, wherein said label includes an explanation as to the reason why said physical progress goal has been updated.

* * * * *